United States Patent [19]

Noguchi et al.

[11] 3,953,500
[45] Apr. 27, 1976

[54] BENZALICYCLIC CARBOXYLIC ACID DERIVATIVE

[75] Inventors: Shunsaku Noguchi, Osaka; Tetsuya Aono, Kyoto; Yoshiaki Araki, Osaka; Kiyohisa Kawai, Kyoto, all of Japan

[73] Assignee: Takeda Chemical Industries, Ltd., Osaka, Japan

[22] Filed: Aug. 12, 1974

[21] Appl. No.: 496,855

[30] Foreign Application Priority Data

| | | |
|---|---|---|
| Aug. 11, 1973 | Japan | 48-90274 |
| Sept. 1, 1973 | Japan | 48-98371 |
| Sept. 13, 1973 | Japan | 48-103602 |
| Sept. 13, 1973 | Japan | 48-103603 |
| Sept. 13, 1973 | Japan | 48-103604 |
| Sept. 13, 1973 | Japan | 48-103606 |
| Oct. 31, 1973 | Japan | 48-122490 |
| May 7, 1974 | Japan | 49-51034 |
| May 24, 1974 | Japan | 49-59017 |
| May 3, 1974 | Japan | 49-62300 |

[52] U.S. Cl. .......... 260/517; 260/268 BC; 260/284; 260/285; 260/293.62; 260/326.5 C; 260/327 M; 260/448 R; 260/456 P; 260/465 D; 260/465 R; 260/465 F; 260/465 G; 260/469; 260/479 R; 260/500.5 H; 260/501.1; 260/471 R; 260/473 F; 260/501.11; 260/515 A; 260/516; 260/518 R; 260/520 C; 260/558 H; 260/558 R; 260/591; 424/308; 424/317; 260/247.7 V; 260/287 K; 260/544 B; 260/590 FA

[51] Int. Cl.² .................... C07C 65/20
[58] Field of Search .......... 260/517, 469, 473 F, 260/471 R, 501.1, 501.11, 448

[56] References Cited
OTHER PUBLICATIONS

Juby et al., Chem. Abstracts Vol. 78 (1973), Abstract No. 52522b.

*Primary Examiner*—James A. Patten
*Attorney, Agent, or Firm*—Wenderoth, Lind and Ponack

[57] ABSTRACT

Compounds of the formula:

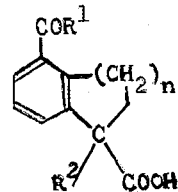

wherein R¹ is an aryl group which may be substituted, R² is hydrogen or a lower alkyl group having 1 to 4 carbon atoms and $n$ is 1 or 2, or derivatives at the carboxyl function thereof, are useful as medicines such as antipyretics, analgesics and anti-inflammatory agents.

20 Claims, No Drawings

BENZALICYCLIC CARBOXYLIC ACID DERIVATIVE

The present invention relates to a novel compound of the following general formula (I):

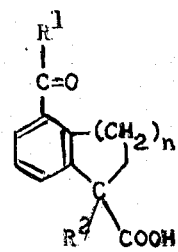

(I)

wherein $R^1$ is an aryl group which may be substituted, $R^2$ is hydrogen or a lower alkyl group having 1 to 4 carbon atoms and $n$ is 1 or 2, or a derivative at the carboxyl function thereof.

The present inventors have made extensive study about a series of indan derivatives and 1,2,3,4-tetrahydro-naphthalene derivatives and succeeded in synthesizing the novel compound of the above formula (I) and a derivative at the carboxyl function thereof, and have found out that the above compounds have remarkable antipyretic, analgesic and anti-inflammatory effects.

The present invention has been accomplished on the basis of this finding.

The principal object of this invention is to provide novel compounds of the formula (I) useful as medicines such as antipyretics, analgesics and anti-inflammatory agents.

Another object of this invention is to provide methods for the production of these novel compounds.

Further objects will be made apparent from the description and claims hereinafter given.

The derivatives at the carboxyl function of compound (I) may be the corresponding ester, acid amide or salt. The esters include alkyl esters whose alkyl moieties are, for example, methyl, ethyl, propyl, iso-propyl, n-butyl, isobutyl, sec.-butyl, tert.-butyl, n-pentyl, n-hexyl, etc., aryl esters such as phenyl ester, etc., aralkyl esters such as benzyl ester, etc.

The acid amides include not only those which carboxyl moieties can be represented by $-CONH_2$ but also the hydroxamic acids represented by $-CONHOH$, the hydrazides represented by $-CONHNH_2$, the N-mono- or di-substituted acid amides corresponding to such organic amines as mono- or di-lower alkylamines of about 1 to about 3 carbon atoms whose alkyl moieties may be substituted by hydroxyl (for example, ethanolamine, diethanolamine, methylamine, ethylamine, dimethylamine, diethylamine, propylamine, etc.), arylamimes (for example, aniline, methylaniline, etc.), five- to six- membered cyclic amines containing 1 to 2 nitrogen atoms (for example, morpholine, pyrrolidine, piperidine, piperazine, N-substituted piperazine, etc.), N-aralkyl-substituted amines (for example, benzylamine, alpha-methylbenzylamine, phenethylamine, etc.), alkyl-substituted or aryl-substituted hydrazines (for example, methyl hydrazine, dimethyl hydrazine, phenyl hydrazine, etc.) and the like. As the salts, there may be mentioned, among others, the salts with alkali metals (for example, sodium, potassium, etc.), alkaline earth metals (for example, calcium, magnesium, etc.) and metals such as aluminum, as well as the ammonium salts and the salts with the organic amines such as those similar to organic amines exemplified as those of the residue for acid amides.

The aryl group represented by $R^1$ includes such species as phenyl, naphthyl, etc., each of which may be further substituted. The substituent or substituents on the aryl group may be any of lower alkyls having 1 to 4 carbon atoms such as methyl, ethyl, propyl, isopropyl, n-butyl, isobutyl, tert.-butyl, etc., lower alkoxy having 1 to 4 carbon atoms such as methoxy, ethoxy, propoxy, isopropoxy, n-butoxy, isobutoxy, tert.-butoxy, etc., halogens such as chlorine, bromine, fluorine etc., mono- or di-alkylamino having 1 to 3 carbon atoms such as N,N-dimethylamino, N,N-diethylamino, N,N-dipropylamino, methylamino, ethylamino, propylamino, etc., acylamino having 2 to 3 carbon atoms such as acetylamino, propionylamino, etc. or acyloxy having 2 to 3 carbon atoms such as acetyloxy, propionyloxy, etc. One or more of these substituents, either the same or different, may occur in optional positions of the aryl group.

The alkyl group designated by $R^2$ may be any straight-chain, branched, saturated or unsaturated alkyl group having 1 to 4 carbon atoms such as methyl, ethyl, propyl, isopropyl, allyl, butyl, isobutyl, tert.-butyl, etc.

The compounds of general formula (I) and the derivatives at the carboxyl function thereof have prominent analgetic, antipyretic, anti-inflammatory and other actions, and show low toxicity and less side effects. Taking advantage of these properties, these compounds can safely be used as analgesics, antipyretics, anti-inflammatory agents and other drugs. When a compound (I) is used as such a medicine, it can be administered, either as it is or in admixture with a pharmaceutically acceptable vehicle, excipient or/and diluent, orally or parenterally in various dosage forms such as powders, granules, tablets, capsules, suppositories and injections. When any of the compounds is used for the purpose of treating such diseases as chronic articular rheumatism, arthritis deformans, spondylosis deformans, arthralgia and lumbago, it is administered orally at the normal daily dose for human adults of about 10 to 1000 mg. or non-orally in amounts of 5 to 500 mg. per dose for adult humans.

The compounds of formula (I) and the derivatives at the carboxyl function thereof can be prepared by the various process steps described below.

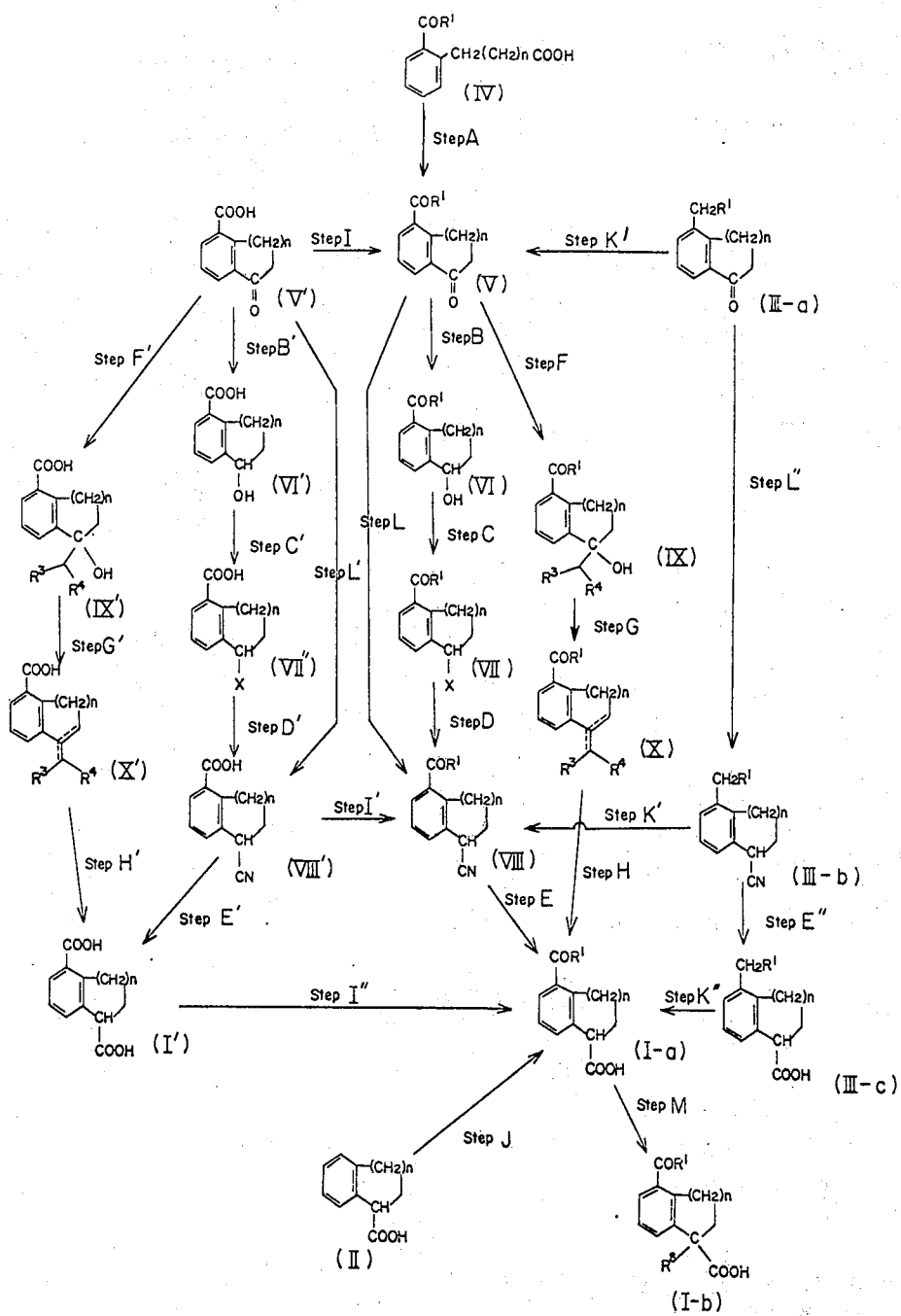

Referring to the above formulas (I-a), (I-b), (III-a), (III-b), (III-c), (IV), (V), (VI), (VII), (VIII), (IX) and (X), $R^1$ has the meaning given above. $R^3$ and $R^4$ in formulas (IX), (IX'), (X) and (X') are each a substituted mercapto group; $R^3$ and $R^4$ together may form a ring. The substituted mercapto group may for example be straight-chain or branched lower alkyl mercapto groups (e.g. methyl-, ethyl-, propyl-, butyl-mercapto, etc.), substituted lower alkylmercapto group (e.g. mercaptoalkyl-, aminoalkyl-mercapto, etc.) arylmercapto groups (e.g. phenylmercapto, etc.), substituted aryl mercapto groups (e.g. p-tolylmercapto, etc.), aralkyl-mercapto group (e.g. benzylmercapto, etc.) or the like. The substituted mercapto groups mentioned above may take the form of S-oxide. $R^8$ in formula (I-b) has the same meaning as alkyl group designated by $R^2$.

Referring to the formulas (VII) and (VII'), X is a hydroxyl group converted to a reactive ester. The hydroxyl group converted to a reactive ester is exemplified by halogens such as chlorine, bromine or iodine and the residues of alkyl-, substituted alkyl-, aryl- and substituted-arylsulfonic acid esters such as methanesulfonic acid ester, trichloromethanesulfonic acid ester, o-toluenesulfonic acid ester, p-toluenesulfonic acid ester, o-nitrobenzenesulfonic acid ester, p-nitrobenzenesulfonic acid ester, o-chlorobenzenesulfonic acid ester, p-chlorobenzenesulfonic acid ester, β-naphthalenesulfonic acid ester, etc.

The reaction of Step A is carried out by subjecting a compound of general formula (IV) or a reactive derivative at the carboxyl function thereof to intramolecular cyclization reaction.

The said reactive derivative of carboxylic acid (IV) may be any one insofar it is instrumental in the attainment of the objects of this step. Thus, for example, acid halides, acid anhydrides, esters, etc. may be mentioned. As the acid halides, there may be mentioned, among others, the corresponding acid chloride, acid bromide, acid iodide and acid fluoride. As said acid anhydride, there may be mentioned, by way of example, the anhydride of carboxylic acid [IV] and the mixed anhydrides of carboxylic acid [IV] and another acid (e.g. organic acids such as formic acid, acetic acid, etc. and inorganic acids such as silicic acid, boric acid, etc.). The ester may for example be the p-nitrophenyl ester of compound (IV).

The intramolecular cyclization reaction according to this invention is generally conducted with advantage in the presence of a catalyst. As said catalyst, any of the catalysts which are commonly useful in Friedel-Crafts reactions, i.e. Friedel-Crafts catalysts, can be utilized.

For example, Lewis acid (e.g. aluminum chloride, aluminum bromide, aluminum fluoride, iron chloride, iron bromide, antimony chloride, antimony bromide, titanium chloride, tin chloride, tin bromide, zinc chloride, zinc bromide, bismuth chloride, boron trifluoride, etc.); mineral acids such as sulfuric acid, phosphoric acid, polyphosphoric acid, etc.; and hydrogen fluoride to name but a few. When a Lewis acid, among said catalysts, is employed, an alkali metal halide (e.g. potassium chloride, sodium chloride, sodium bromide, potassium bromide, sodium iodide, potassium iodide), for instance, may be added to the reaction system. While the proportion of such a catalyst is more or less optional, it is preferably in the range of about 1 to 10 moles to each mole of carboxylic acid (IV) or its reactive derivative. It should, however, be understood that when said mineral acid or hydrogen fluoride is employed as the catalyst, it may be used in large excess so that the catalyst will function as the solvent as well. The reaction of this step may be carried out in the absence of a solvent or in the presence thereof. The solvent for this purpose may be any solvent only if it is inert to the contemplated reaction. Thus, nitrobenzene and halogenated hydrocarbons (e.g. methylene chloride, ethylene chloride, 1,1,2,2-tetrachloroethane, chlorobenzene, dichlorobenzene, etc.) may be mentioned by way of example. While the reaction conditions including the reaction temperature and time are more or less optional, the preferred temperature range is from room temperature to about 200°C.

The compound of general formula (V) thus obtained can be easily isolated and purified by conventional separation-purification procedures such as extraction, distillation, recrystallization, chromatography, etc.

The reaction of Step B is carried out by reducing a compound of the general formula (V).

This reduction can be achieved by any procedure for reducing a carbonyl group to an alcohol. For practical purposes, there may be exemplified several kinds of the reduction procedures, namely, the reduction procedure involving the use of a metal hydride such as sodium borohydride or lithium aluminum hydride, the catalytic reduction procedure which involves the use of a metal catalyst such as palladium, nickel, platinum, iron, rhodium, iridium or the like; the reduction procedure involving the use of an alkali metal, e.g. sodium, lithium, potassium or the like together with a solvent which can act as hydrogen donor, e.g. alcohol, liquid ammonia or the like; and the reduction procedure in which a metal complex compound of a metal such as rhodium, iridium or the like is employed. While each of these reduction procedures generally proceed under cooling to heating and the reaction temperature and time are not particularly critical, the preferred temperature range is from about −35° to about 100°C.

In the case of catalytic reduction, hydrogen is introduced at normal pressure or at elevated pressure, there being no particular limitation upon the pressure of hydrogen. When lithium aluminum hydride is employed, it is preferable to use anhydrous ether solvents (e.g. ethyl ether, propyl ether, isopropyl ether, tetrahydrofuran, dioxane, ethylene glycol-dimethyl ether, ethylene glycol-diethyl ether, etc.), while liquid ammonia and dry alcohols (e.g. methanol, ethanol, propanol, isopropanol, butanol, isobutanol, etc.), among others, are suited when alkali metals are employed. In other cases, water, alcohols, ethers, etc. are used, although there is no particular limitation upon the type of solvent unless such a solvent do not hinder the contemplated reduction. The compound of general formula (VI) thus obtained can be isolated and purified by per se known procedures such as distillation, recrystallization, column chromatography, etc.

The reaction of Step C is carried out by subjecting a compound of the formula (VI) to a reaction leading to a reactive ester to obtain a compound of formula (VII).

As regards the reaction leading to a reactive ester, there may be mentioned halogenation and reactions leading to sulfonic acid esters.

The halogenation reaction may be conducted by, for example, the procedure wherein a hydrogen halide in anhydrous conditions or an aqueous solution (e.g. hydrogen chloride gas, hydrogen bromide gas, hydrochloric acid, hydrobromic acid, hydroiodic acid, etc.); a thionyl halide (e.g. thionyl chloride, thionyl bromide, thionyl iodide, etc.); a phosphorus halide (e.g. phosphorus pentachloride, phosphorus trichloride, phosphorus tribromide, phosphorus triiodide, etc.); phosphorus oxychloride; red phosphorus and a halogen such as bromine or iodine; an alkali metal iodide (e.g. sodium iodide, potassium iodide, etc.) and phosphoric acid, among others, is/are permitted to act, either alone or in combination, upon compound (VI). The reaction may be conducted in the presence or absence of a catalyst. The catalyst is generally selected from among organic amines, e.g. pyridine, aromatic amines (e.g. dimethylaniline, diethylaniline, etc.) and aliphatic amines (e.g. triethylamine etc.).

The reaction proceeds in the presence or absence of a solvent. The solvent, if employed, may be any type of solvent insofar as it is inert to the reaction. Examples of the solvent inert to the reaction include benzene, toluene, xylene, chlorobenzene, hexane, halogenated hydrocarbons (e.g. chloroform, methylene chloride, ethylene chloride, 1,1,2,2-tetrachloroethane, etc.). While the reaction temperature depends upon the reagents and solvent, if any, to be employed, the reaction generally proceeds over the temperature range of under cooling to under heating, preferably at about 0° to about 100°C, there being no particular restriction on the reaction time.

When the alcohol of general formula (VI) is to be converted to a sulfonic acid ester, the sulfonic esterification reaction is employed. For example, the sulfonic acid or sulfonyl chloride corresponding to one of the sulfonic acid esters mentioned in the definition of X in compound (VII) is reacted with the alcohol of general formula (VI). While the reaction proceeds in the absence of a catalyst, it can be conducted more advantageously in the presence of a catalyst. As the catalyst, a basic catalyst is ordinarily employed. More common species of the catalyst are dimethylformamide and pyridine as well as the aromatic amines and aliphatic amines mentioned in halogenation of this step. As regards the solvent, such a basic agent may be used in a large excess so that it will function as the solvent as well. It is also possible to employ solvents inert to the reaction such as benzene, toluene, xylene, chlorobenzene, hexane, halogenated hydrocarbons (e.g. chloroform, methylene chloride, ethylene chloride, 1,1,2,2-tetrachloroethane, etc.). While the reaction temperature and time are virtually optional, the preferred temperature range is from about 0° to about 50°C.

The compound (VII) thus obtained can be separated and purified by a per se known separation purification procedures such as recrystallization, distillation, chromatography, etc.

The reaction of Step D is carried out by reacting a compound of the general formula (VII) with a cyanide.

As the cyanide to be reacted with compound (VII), there may be mentioned the salts of metals of Group I of the Periodic Table of the Elements. Thus, for example, the sodium salt, potassium salt, copper salt, silver salt, etc. can be employed.

The reaction may be generally carried out in the absence or presence of a catalyst. As said catalyst, there may be mentioned quaternary ammonium halides. The quaternary ammonium ions may be substituted by alkyl groups of about 1 to 20 carbon atoms. Among them are those comprising a straight-chain or branched alkyl group including, for example tetraalkylammonium, alkylaralkylammonium, tetraaralkylammonium, etc. For example, tetrabutylammonium, triethylhexadecylammonium, triethylbenzylammonium, etc. may be mentioned. More common species of halide ion are chloride, bromide, etc. Further, instead of using a cyanide and the catalyst, use may be made of an ammonium cyanide. In this connection, the ammonium ion may be any of the above-mentioned ammonium ions.

While the reaction time, temperature and other conditions are not particularly critical, the reaction temperature is preferably in the range of about 0° to about 100°C. As the solvent to be employed when the reaction is to be carried out without a catalyst, it is advantageous to employ, for example, the following: dimethylsulfoxide, N,N-dimethylformamide, hexamethylphosphoric triamide, alcohols (e.g. methanol, ethanol, propanol, isopropanol, etc.), acetone and water. When use is made of an ammonium cyanide or a solvent, it is advantageous to use water as the solvent.

The resultant compound of general formula (VIII) can be separated and purified by per se known procedures such as distillation, recrystallization, chromatography, etc.

The reaction of Step E is carried out by subjecting a compound of the general formula (VIII) to solvolysis.

The solvolysis may generally be hydrolysis with water as the solvent or alcoholysis with an alcohol as the solvent.

Aside from them, there are cases in which a phenol, for instance, is used as the solvent. The solvolysis is generally conducted in the presence of a catalyst, examples of which include hydrogen halides (e.g. hydrogen chloride, hydrogen bromide, hydrogen iodide), mineral acids such as hydrochloric acid, hydrobromic acid, hydriodic acid, sulfuric acid, phosphoric acid, polyphosphoric acid, etc.; organic acids such as formic acid, acetic acid, p-toluenesulfonic acid, β-naphthalenesulfonic acid, etc.; Lewis acids mentioned in the explanation of Step A; alkali metal hydroxide such as sodium hydroxide, potassium hydroxide, etc.; alkaline earth metal hydroxide such as calcium hydroxide, barium hydroxide, etc.; metal alcoholates made up of lower alcohols comprising alkyls of about 1 to 4 carbon atoms (e.g. methanol, ethanol, propanol, isopropanol, butanol, isobutanol, sec.-butanol, tert-butanol, etc.) with alkali metals such as sodium, potassium, etc.; hydrogen peroxide, per-acids such as peracetic acid, perbenzoic acid, etc. These catalysts are at times used alone and at other times used in combination. While the reaction temperature varies with the type of catalyst used, the reaction may generally be carried out under cooling, at room temperature or under heating, preferably at about 0° to about 100°C. The reaction time is virtually optional. The structure of product (I-a) depends upon the reaction conditions used and the reaction conditions may be selected according to the contemplated compound.

For example, when use is made of an alcohol as the solvent for compound of general formula (VIII) and of a hydrogen halide, e.g. hydrogen chloride, hydrogen bromide, etc., sulfuric acid, p-toluenesulfonic acid or the like as the catalyst, there is obtained a compound (I-a) whose carboxyl group is converted to the ester corresponding to alcohol used. When a compound (VIII) is hydrolyzed with water, there is obtained a compound (I-a) whose carboxyl group is converted to an carbamoyl group ($-CONH_2$), and under severe conditions, the acid amide is further hydrolyzed to give a compound (I-a) whose carboxyl group is in the form of free acid. In this procedure, one may of course isolate the acid amide formed and, then, hydrolyze it into carboxylic acid.

The acid amide is obtained when concentrated sulfuric acid, a concentrated solution of hydrogen halide or the like is employed as the catalyst under cooling, when polyphosphoric acid is used as the catalyst under heating; or when boron trifluoride is employed at room temperature, to name but a few instances. There is obtained a compound (I-a) whose carboxyl group is free when use is made of sulfuric acid, an alkali metal hydroxide or the like under heating. When compound (VIII) is solvolyzed with a solvent other than water, there are cases, according to the conditions used, in which the free acid is directly produced, bypassing the formation of acid amide.

The compound of general formula (I-a) which has been produced by the reaction of this step can be purified by per se known separatory procedures such as recrystallization, distillation, chromatography, etc.

When the resultant product compound is a free carboxylic acid of general formula (I-a), the resultant product compound can be converted to derivatives at its carboxyl function by procedures which are known per se (e.g. the production of salts by neutralization or other procedure; esterification by means of an alcohol in the presence of acid, amidation which comprises reacting the compound with an amine; and amidation which comprises the steps of converting the compound to an acid halide and, then, reacting the latter with an amine). Conversely, such a derivative at the carboxyl function can be converted to the free carboxylic acid by procedures which are known per se (e.g. hydrolysis in the presence of base or acid). Said derivative at the carboxyl function can be further converted to other types of derivatives by procedures which are known per se (e.g. amidation which comprises reacting the ester with an amine; esterification which comprises reacting the amide with an alkyl polyphosphate; etc.).

The cyclic carboxylic acid of general formula (I-a) which is obtainable by the method hereinbefore described has an asymmetric carbon atom in 1-position of its molecule and, therefore, can be resolved through a method known per se into optical isomers, i.e. d- and l-compounds.

Thus, optically active forms of the free carboxylic acid derivatives can be isolated by the steps of dissolving the racemic free acid in a suitable inert solvent such as chloroform, acetone, benzene, hexane, ether, water, methanol, ethanol, acetonitrile or the like, reacting the same with an optically active base, separating the resultant salt or amide into diastereoisomers by taking advantage of their dissimilarity in solubility and, then, treating them with an acid. The optically active free carboxylic acid can also be isolated by the steps of preparing an ester from the racemic free acid and a suitable optically active alcohol, resolving the ester into diastereoisomers by a procedure which is known per se such as recrystallization, distillation or chromatography and, then, hydrolyzing the ester with an acid or a base. The optically active base to be thus used is exemplified by basic amine such as quinine, brucine, cinchonidine, cinchonine, dehydroabietylamine, hydroxyhydrindamine, menthylamine, morphine, $\alpha$-phenylethylamine, phenyloxynaphtylmethylamine, quinidine, strychnine, etc., basic amino acid such as lysine, arginine, etc., ester of amino acid, etc.

The optically active alcohol is exemplified by borneol, menthol, 2-octanol, etc.

The cyclic carboxylic acid derivative of general formula (I-a) which has been obtained by an optical resolution procedure such as those described above can be converted to an optically active derivative at its carboxyl function by the above-mentioned procedures which are known per se.

The Steps B',C', D' and E' are carried out by taking the similar procedures to those of Steps B, C, D and E, respectively. In theses cases, the compounds (V'), (VI'), (VII') and (VIII') used as starting compounds in each of Steps B', C', D' and E' may be derivatives at the carboxyl function thereof. As the derivatives at the carboxyl function, there are mentioned those defined in the definition of the derivatives at the carboxyl function of compound (I).

The Step E'' is carried out by taking the similar procedures to those of Step E.

The reaction of Step F is carried out by reacting a compound (V) with a compound of general formula:

$$R^3 - CH_2 - R^4 \qquad (XI)$$

wherein $R^3$ and $R^4$ have the meanings given above.

As compounds of formula (XI), there are mentioned 1,3-dithian, 1,3,5-trithian, methyl methylthiomethylsulfoxide, methyl methylthiomethylsulfide, ethyl ethylthiomethylsulfoxide, ethyl ethylthiomethylsulfide and the like.

This reaction is conveniently conducted in the presence of a base. As said base, there may be mentioned, by way of example, alkali metal hydroxide (sodium hydroxide, potassium hydroxide, etc.), alkali metal hydride (e.g. sodium hydride, lithium hydride, etc.), alkali metal alcoholate (e.g. sodium methylate, sodium ethylate, sodium tert-butylate, potassium tert.-butylate, sodium tert.-amylate, etc.), alkali metal amide (e.g. sodium amide, potassium amide, lithium amide, sodium piperidide, potassium piperidide, lithium piperidide, sodium diethyl amide, potassium diethylamide, lithium diethylamide, sodium diisopropylamide, potassium diisopropylamide, lithium diisopropylamide, lithium bis-trimethylsilylamide, lithium dicyclohexylamide, etc.), n-butyl lithium, triton-B, etc.

This reaction is generally conducted in the presence of a solvent. Virtually any solvent can be used for this purpose, only if it is inert to the reaction. For example, ethers (e.g. diethyl ether, tetrahydrofuran, dioxane, 1,2-dimethoxyethane, 1,2-diethoxyethane, diethylene glycol dimethyl ether, etc.), benzene, toluene, xylene, methanol, ethanol and water can be employed with advantage.

While the amount of compound (XI) and that of the base are largely optional, it is desirable to each of them in the proportion of about 1 to about 2 moles per mole of compound (V).

The reaction temperature may preferably range from about $-30°C$ to the boiling point of the solvent used and the reaction time is preferably about 5 to 25 hours.

The compound (IX) thus obtained can easily be isolated by a conventional method known per se.

The reaction of Step G is carried out by subjecting a compound (IX) to dehydration.

In the dehydration, use may be made of dehydrating agent with advantage. As the dehydrating agent for this reaction, there may be used, with advantage, mineral acids (e.g. sulfuric acid, phosphoric acid, phosphorous acid, hydrochloric acid, etc.), phosphorus oxychloride, thionyl chloride, arylsulfonic acids (e.g. benzenesulfonic acid, p-toluenesulfonic acid, $\beta$-naphthalenesulfonic acid, etc.), acetic acid and its derivatives (e.g. trifluoroacetic acid, trichloroacetic acid, etc.) and lower alkylsulfonic acid (e.g. methanesulfonic acid, ethanesulfonic acid, propanesulfonic acid, etc.), to name but a few. The solvent to be used for the purpose may be virtually any type of solvent insofar as it does not interfere with the reaction. The reaction temperature may be a reduced temperature, i.e. under cooling, to about 150°C, the reaction temperature being more or less optional.

The compound of formula (X) thus obtained may assume the two structures shown below as (X-a) and (X-b).

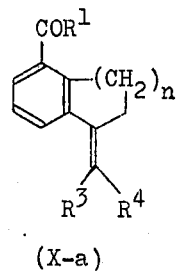 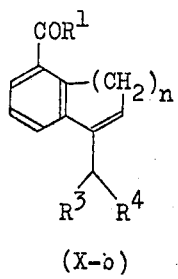

(X-a)   (X-b)

The reaction of Step H is carried out by subjecting a compound (X) to solvolysis.

The solvolysis generally refers to hydrolysis with water as the solvent, or alcoholysis which employs as the solvent an alcohol (e.g. methanol, ethanol, propanol, isopropanol, butanol, isobutanol, sec.-butanol, tert.-butanol, benzyl alcohol, etc.), although phenol, for one, may also be used as the solvent.

The solvolysis is generally conducted in the presence of a catalyst. As said catalyst, there may be employed hydrogen halide (e.g. hydrogen chloride, hydrogen bromide, hydrogen iodide, etc.); mineral acids such as hydrochloric acid, hydrobromic acid, hydriodic acid, sulfuric acid, phosphoric acid, polyphosphoric acid, etc.; organic acids such as formic acid, acetic acid, p-toluenesulfonic acid, β-naphthalenesulfonic acid, etc.; heavy metal salts (e.g. mercury chloride; mercury bromide, mercury fluoride, mercury sulfate, copper chloride, copper bromide, etc.); to name but a few. These catalyst are at times used alone or used at other times in a combination of two or more. While the reaction temperature depends upon such reaction conditions as the types of solvent and catalyst, the reaction may generally be carried out under cooling, at room temperature or under heating, preferably at about 0 to about 120°C.

The reaction time is optional for all practical purposes. The desired compound (I-a) of this reaction is obtained in various forms at the carboxyl function thereof under the influence of reaction conditions. The desired compound (I-a) having the desired species of derivative at the carboxyl function can be obtained by selecting the proper reaction conditions. For example, when compound (X) is hydrolyzed, the resultant product (I-a) is in the form of free acid. Alcoholysis of compound (X) gives a compound (I-a) whose carboxyl group is an esterified carboxyl group corresponding to the alcohol used. Further by selecting reaction conditions of said solvolysis, there can also be obtained contemplated compound (I-a) such that the carboxyl group in compound (I-a) has been esterified or de-esterified.

The compounds (I-a) can be resolved into optical isomers by per se known procedures which may be referred to those mentioned in Step E.

The Steps F', G' and H' are carried out by taking the similar procedures to those of Steps F, G and H, respectively. In these cases, the compounds (V'), (IX') and (X') used as starting compounds in each of Steps F', G' and H' may be derivatives at the carboxyl function thereof. As the derivatives at the carboxyl function, there are mentioned those defined in the definition of the derivatives at the carboxyl function of compound (I).

The reaction of Step I is carried out by reacting a compound of formula (V') with a compound of general formula $$R^1 - H \qquad (XII)$$

wherein $R^1$ has the meaning given above.

The starting compound (V') may be a reactive derivative at the carboxyl function thereof. As the reactive derivative at the carboxyl function, there are mentioned a derivative at the carboxyl function defined in the starting compounds in Step B' as well as p-nitrophenyl ester and acid halide such as acid chloride, acid bromide, acid iodide, etc. When compound (V') is a free carboxylic acid, it may first be converted to a reactive derivative at the carboxyl function and, then, the derivative be subjected to the contemplated reaction. When compound (V') is a reactive derivative, it may first be converted to the free carboxylic acid which, in turn, is subjected to the contemplated reaction. This reaction is generally conducted with advantage in the presence of a catalyst which may be any of the agents that can ordinarily be used as catalysts in Friedel-Crafts reactions, that is to say any of the so-called Friedel-Crafts catalysts. Thus, metal halides (e.g. aluminum chloride, aluminum bromide, aluminum fluoride, iron chloride, iron bromide, antimony chloride, antimony bromide, titanium chloride, tin chloride, tin bromide, zinc chloride, zinc bromide, bismuth chloride, etc.); Lewis acids such as boron fluoride; mineral acids such as sulfuric acid, phosphoric acid, polyphosphoric acid, etc.; hydrogen fluoride; etc. may be mentioned by way of example. The reaction is advantageously conducted in the presence of a solvent which may be an aromatic compound of general formula (XII) or any of the solvents inert to the reaction. Said solvents inert to the reaction include, among others, carbon disulfide, nitrobenzene, halogenated hydrocarbons (e.g. methylene chloride, ethylene chloride, 1,1,2,2-tetrachloroethane, etc.), etc.

When sulfuric acid, polyphosphoric acid or hydrogen fluoride, for instance, is used as the catalyst, it can be used in a large excess so that it will function as the solvent as well. When a Friedel-Crafts catalyst is employed, its proportion is ordinarily about 1 to 6 moles per mole of the carboxylic acid of general formula (V') or its reactive derivative. While the reaction conditions such as temperature and time are not particularly critical, the practically desirable reaction temperature is somewhere between −15°C and the neighborhood of the boiling point of the solvent used. The temperature may be increased or decreased within the above range. The reaction time ordinarily ranges from about 1 to 5 hours, although it depends upon the species of starting compound, catalyst and solvent. The resultant compound of general formula (V) can be separated and purified by procedures which are known per se, such as distillation, recrystallization, column chromatography, etc.

The Steps I' and I'' is carried out by taking a similar procedure to that of Step I.

In these Steps, the starting compounds may be reactive derivatives at the carboxyl function on benzene ring of compound (VIII') or (I'). As the reactive derivatives, there are mentioned those defined in the starting compound in Step I. Further, the starting compound (I') of Step I'' may be derivative at the carboxyl function other than that on benzene ring. As the derivative, there are mentioned those defined in compound (I).

Though, in the reaction of Step I'', there is produced a mixture of compound (I-a) and compounds of following formula:

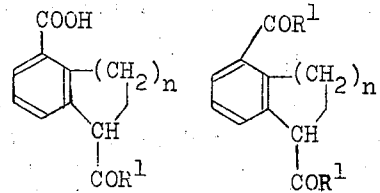

wherein $R^1$ has the meanings given above, the contemplated compound (I-a) can be separated and purified by per se known separatory procedures such as recrystallization, distillation, chromatography, etc.

The compounds (I-a) can be obtained in a suitable form such as free acid, ester, salt and the like by taking the procedures mentioned in Step E.

Further, the compounds (I-a) can be resolved into optical isomers by a similar manner to that described in Step E.

The reaction of Step J is carried out by reacting a compound of general formula (II) with a compound of general formula;

$$R^1 - COOH \tag{XIII}$$

wherein $R^1$ has the meaning given above.

The compound (II) may be a derivative at the carboxyl function thereof. As the derivative at the carboxyl function, there are mentioned those defined in compound (I). The compound (XIII) may be a reactive derivative at the carboxyl function thereof. As the reactive derivative at the carboxyl function, there are mentioned those defined in the starting compound (IV) of Step A. The proportion of said carboxylic acid of general formula (XIII) or said reactive derivative of (XIII) is preferably about 1 to about 10 moles to each mole of said carboxylic acid of general formula (II) or derivative at the carboxyl function of (II) for practical purposes.

Generally speaking, the reaction is advantageously conducted in the presence of a solvent and a catalyst. The solvent may be any solvent that is inert to the reaction; for example, carbon disulfide, nitrobenzene, halogenated hydrocarbons (for example, methylene chloride, ethylene chloride, 1,1,2,2-tetrachlorethane, chlorobenzene, dichlorobenzene, etc.) and so forth. As the catalyst for this reaction, use may be made of the substances which can be ordinarily used as catalysts in Friedel-Crafts reactions, i.e. the so-called Friedel-Crafts catalysts. While the proportion of such catalyst usually need not be over about 1 to 1.5 moles per mole of said carboxylic acid of general formula (XIII) or said reactive derivative thereof, any of the above-mentioned mineral acids, hydrogen halide, etc. may be used in large excess so that it will function as the solvent as well. The reactive conditions such as temperature and time are largely optional.

However, for practical purposes, the reaction temperature ordinarily ranges from −15°C to the boiling point of the solvent employed and the reaction system may be cooled or heated to a suitable extent within said temperature range. Ordinarily the reaction time is about 1 to about 4 hours, although it depends upon the species of starting compounds, catalyst and solvent used.

The reaction of this invention gives rise not only to the contemplated compound (I-a) or a derivative at the carboxyl function of (I-a) but at times to a compound of general formula:

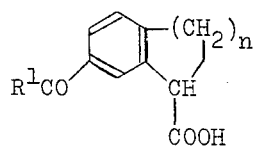

(XIV)

wherein $R^1$ and n have the meanings given above.

The compounds (I-a) can be separated and purified by a per se known separatory procedures such as recrystallization, distillation and chromatography.

The compound (I-a) can be obtained in a suitable form such as free acid, ester, salt, etc. by taking the procedures mentioned in Step E.

Further, the compound (I-a) can be resolved into optical isomers by a similar manner to that described in Step E.

The reaction of Step K is carried out by oxidizing a compound (III-a).

As the procedures of oxidation, use may be made of any procedure by which a methylene group can be oxidized to a carbonyl group. Thus, oxidation procedures utilizing for example, chromic acid, permanganic acid, manganese dioxide, selenium dioxide, cerium, N-bromosuccinimide, etc. as the oxidizing agents may be used to advantage. More particularly, in the chromic acid oxidation process, use may be made, with advantage, of any of such oxidizing agents as chromic anhydride, chromic acid, dichromates (e.g. ammonium dichromate, potassium dichromate, sodium dichromate, etc.), chromates (e.g. ammonium chromate, potassium chromate, silver chromate, cobalt chromate, cesium chromate, sodium chromate, barium chromate, etc.), chromic acid chloride (e.g. chromyl chloride), etc. The solvent for use in this process may for example be an acid, e.g. sulfuric acid, acetic acid or the like; water; and an organic solvent, e.g. acetone, benzene, ether, acetic anhydride or the like. These solvents are used either alone or as a mixture. In the permanganic acid oxidation, use is desirably made of such oxidizing agents as permanganates (e.g. potassium permanganate, sodium permanganate, barium permanganate, calcium permanganate, magnesium permanganate, zinc permanganate, etc.). As the reaction solvent, a basic, neutral or acid aqueous solution is desirable and, in certain cases, an organic solvent such as acetone, benzene or toluene may be concomitantly present. In the manganese dioxide oxidation, manganese dioxide and sulfuric acid are desirably used as the oxidizing agent and solvent, respectively. The selenium dioxide oxidation is desirably carried out with selenium dioxide as the oxidizing agent in water, acetic anhydride, acetic acid, dioxane or the like as the solvent. In the case of cerium oxidation, cerium ammonium nitrate $[Ce(NH_4)_2(NO_3)_6]$ is used as the oxidizing agent, the solvent being either a single-component solvent or a solvent mixture, for example, water, mineral acids (e.g. perchloric acid, nitric acid, sulfuric acid, etc.), organic acids (e.g. formic acid, acetic acid, propionic acid, etc.), acetonitrile, tetrahydrofuran, acetone, dioxane, etc. may be employed for this purpose.

In these oxidizing reactions, the reaction temperature is somewhere within the range of under cooling with ice to about 100°C, the reaction time being more or less optional.

The contemplated compound thus obtained can be separated and purified by procedures which are known per se, such as distillation, recrystallization, column chromatography, etc.

The Steps K' and K'' are carried out by taking the procedures similar to those of Step K:

In the reaction of Step K'', the starting compound may be a derivative at the carboxyl function of compound (III-c). As the derivative, there are mentioned those defined in compound (I).

The objective compounds of these reactions can be separated and purified by the per se known separatory procedures such as recrystallization, distillation and chromatography.

The compound (I-a) can be recovered in a suitable form such as free acid, ester, salt, etc. by taking the procedures mentioned in Step E.

Further, the compound (I-a) can be resolved into optical isomers by such a per se known manner as described in Step E.

The reaction of Step L is carried out by reacting a compound of general formula (V) with sulfonylmethylisonitrile compound.

Said sulfonylmethylisonitrile compound may for example be a compound represented by general formula $$R^9SO_2CH_2NC \qquad (XV)$$

wherein $R^9$ means an aryl, aralkyl or alkyl group. The aryl group stands for, for example, phenyl or naphthyl whose aromatic nucleus may be substituted by alkyls (e.g. methyl, ethyl, etc.), halogens (e.g. chlorine, bromine, etc.), alkoxys (e.g. methoxy, etc.), etc. in optional positions. Particularly advantageous for practical purposes are phenyl, p-tolyl, etc. The aralkyl group represented by $R^9$ may for example be benzyl or phenethyl; the alkyl group which is also represented by $R^9$ may for example be methyl, ethyl n-propyl, isopropyl n-butyl, isobutyl, sec.-butyl, tert.-butyl or the like.

This reaction consists in reacting 1 to 1.5 moles of (XV) with each mole of (V) in the presence of substantially 1 to 3 moles per mole of (V) of a base in a solvent. Preferred species of the solvent are mixtures of ethers such as dimethoxyethane, diethoxyethane, tetrahydrofuran, etc., with lower alcohols such as methanol, ethanol, tert.-butanol, etc., and the mixing ratio is preferably 2 to 20 parts of such an ether to each part of an alcohol and, for better results, within the range of 5 to 10 parts to 1 part. The base is exemplified by metal alcoholates which are obtainable from lower alcohols, e.g. methanol, ethanol, t-butanol, etc., and alkali metals, e.g. sodium, potassium, etc. In the presence of such a base, the reaction proceeds with increased advantage.

The reaction temperature is selected from within the range of 0° to 100°C according to the reactivity of the starting compounds and the types of solvent, base, etc. to be used. Particularly preferred is a temperature which lies somewhere between 10° and 40°C.

Generally, the reaction goes to conclusion in 1 to 6 hours.

The desired product (VIII) can be isolated by per se known procedures.

The Steps L' and L'' are carried out by taking the procedures similar to those of Step L.

The starting compound of Step L' may be a derivative at the carboxyl function of compound (V'). As the derivative at the carboxyl function, there are mentioned those defined in the starting compound (V') of Step B'.

The reaction of Step M is carried out by subjecting a compound of general formula (I-a) to alkylation.

The alkylation is conducted by reacting with the compound (I-a) with a compound of general formula $$R^8 - X \qquad (XVI)$$

wherein $R^8$ is an alkyl having 1 to 4 carbon atoms and X has the meaning given above.

As the alkyl shown by $R^8$, there are mentioned methyl, ethyl, propyl, i-propyl, allyl, n-butyl, isobutyl, sec.-butyl, tert.-butyl, etc.

This reaction proceeds with advantage in the presence of a base. As the base, there are mentioned alkali metal hydroxide (e.g. sodium hydroxide and potassium hydroxide), alkali metal hydride (e.g. sodium hydride and lithium hydride), alkali metal alcoholate (e.g. sodium methylate, sodium ethylate, sodium tert.-butylate, potassium tert.-butylate and sodium tert.-amylate), alkali metal amide (e.g. sodium amide, potassium amide, lithium amide, sodium piperidide, potassium piperidide, lithium piperidide, sodium diethylamide, potassium diethylamide, sodium diisopropylamide and lithium diisopropylamide), etc. As the solvent to be used, there are mentioned alcohols (e.g. methanol, ethanol, propanol, butanol and tert.-butanol), ethers (e.g. diethylether, tetrahydrofuran, dioxane, methoxyethane, 1, 2-di-1,2 diethoxyethane, 1,2-dimethoxyethane, dimethylether), benzene, toluene, xylene, dimethylsulfoxide, N,N-dimethylformamide, hexamethylphosphoric triamide, liquid ammonia, diethylamine, diisopropylamine, etc.

The base is usually used in an amount of 1 to 10 moles per mole of compound (I-a) and compound (XVI) is usually used in an amount of 1 to 3 moles per mole of a base. While the reaction conditions such as temperature and time are largely optional, the preferred temperature range is about 0° to about 50°C.

The compound (I-b) thus obtained can be separated and purified by per se known separation-purification procedures such as recrystallization, distillation, chromatography, etc.

The compounds (I-b) can be recovered in optional form such as free acid, ester, salt and the like by taking similar procedures to those mentioned in Step E.

Further, the compounds (I-b) can be resolved into optical isomers by a similar manner to that described in Step E.

Throughout the present specification the abbreviations "mg.," "g.," "ml." and "°C", respectively refer to "milligram(s)," "gram(s)," "milliliter(s)" and "degree(s) centigrade."

Although the following examples are further illustrative of this invention, these do not have any meaning of limiting or restricting the scope of this invention at all.

REFERENCE EXAMPLE 1

To 100 ml. of methylene chloride is added 50 g. of dry aluminum chloride. The mixture is stirred and 28 g. of benzoyl chloride is added dropwise. While the solution is stirred at 30°–40°C, 16.4 g. of methyl β-phenylpropionate is added dropwise over a period of about 1 hour. After the drop-by-drop addition has been completed, the solution is stirred at 30°–40°C for 2 hours. After cooling, the solution is poured into ice-hydrochloric acid and extracted with methylene chloride. The extract is washed with dilute hydrochloric acid, water, dilute aqueous sodium hydroxide and water in the order mentioned, followed by drying. The solvent is distilled off under reduced pressure and the residue is purified by column chromatography (1 kg. of silica gel; eluted with benzene). The described procedure gives methyl p-benzoyl-β-phenylpropionate and methyl o-benzoyl-β-phenylpropionate.

To a solvent mixture of 20 ml. of ethanol and 100 ml. of water are added 20 g. of the methyl o-benzoyl-β-phenylpropionate thus obtained and 15 g. of potassium hydroxide. The mixture is refluxed for 2 hours. After cooling, the solvent is distilled off and the residue is diluted with water and washed with ether. The aqueous layer is acidified with hydrochloric acid and extracted with ether. The extract is washed with water and dried. Then, the solvent is distilled off and the residue is crystallized from benzene-hexane. The prodedure gives o-benzoyl-β-phenylpropionic acid.

REFERENCE EXAMPLES 2–6

By the similar manner to Reference 1, following compounds are produced.

| Reference example | Produced-compound | Starting compound |
|---|---|---|
| 2 | o-(p-toluoyl)-β-phenyl-propionic acid | p-toluoyl chloride + methyl β-phenyl-propionate |
| 3 | o-(p-chlorobenzoyl)-β-phenylpropionic acid | p-chlorobenzoyl chloride + methyl β-phenyl-propionate |
| 4 | o-benzoyl-γ-phenyl-butylic acid | ethyl γ-phenyl-butylic acid + benzoyl chloride |
| 5 | o-(p-toluoyl)-γ-phenylbutylic acid | ethyl γ-phenyl-butylic acid + p-toluoyl chloride |
| 6 | o-(p-chlorobenzoyl)-γ-phenylbutylic acid | ethyl γ-phenyl-butylic acid + p-chlorobenzoyl chloride |

REFERENCE EXAMPLE 7

To 700 ml. of ice-cooled dry ether is added 15 g. of lithium aluminum hydride, followed by the addition of 61.8 g. of crystalline o-(p-chlorobenzyl)benzoic acid. The mixture is refluxed with stirring for 5 hours, after which it is allowed to stand at room temprature overnight and, then, the excess reagent is decomposed with ice-water. The organic layer is separated, washed with water and dried. The solvent is distilled off under reduced pressure and the residue is distilled under reduced pressure. The procedure gives o-(p-chlorobenzyl)benzyl alcohol as a fraction boiling at 145°–155° C/0.1 mm mercury.

In 400 ml. of chloroform is dissolved 46.5 g. of o-(p-chlorobenzyl)benzyl alcohol and, under stirring and cooling with ice, 19 g. of phosphorus tribromide is added dropwise. After the drop-by-drop addition has been completed, the mixture is stirred under cooling with ice for 1 hour and, then, at room temperature for 1 hour. The solution is allowed to stand overnight and washed three times with ice cooled water, followed by drying over calcium chloride. The solvent is distilled off under reduced pressure, whereupon o-(p-chlorobenzyl)benzyl bromide is obtained as an oily residue. This product is used in the next reaction without purification.

In 100 ml. of ethanol is dissolved 4.8 g. of sodium metal and while the solution is stirred at room temperature, 64 g. of diethyl malonate is added dropwise. After the drop-by-drop addition has been completed, the mixture is heated at 80°–90°C for 15 minutes and, then, cooled. Under stirring, a mixture of 59 g. of o-(p-chlorobenzyl)benzyl bromide and 150 ml. of dry benzene is added dropwise. After the dropwise addition has been completed, the mixture is refluxed with stirring for 2 hours. The solvent is distilled off under reduced pressure and the residue is diluted with water and extracted with benzene. The extract is washed with water and dried. The solvent is then distilled off under reduced pressure and the residue is further distilled under reduced pressure. The described procedure gives diethyl o-(p-chlorobenzyl)benzylmalonate as a fraction boiling at 175°–185°C/0.2 mm mercury.

In 70 ml. of water is dissolved 25 g. of potassium hydroxide, followed by the addition of 62.5 g. of diethyl o-(p-chlorobenzyl)benzylmalonate. The mixture is refluxed under stirring for 6 hours and, then, allowed to stand at room temperature overnight. To the reaction mixture is added 300 ml. of water and, after the mixture is rendered acidic by the addition of hydrochloric acid, it is cooled with ice.

The precipitate is collected and dissolved in a solvent mixture of ethyl acetate and ether. The solution is washed with aqueous sodium chloride and dried. The solvent is distilled off under reduced pressure, whereupon o-(p-chlorobenzyl)benzylmalonic acid is obtained.

Without purification, this product is decarboxylated by heating at 160°–170°C for 3 hours, after which it is cooled. Recrystallization from cyclohexane gives 3-[o-(p-chlorobenzyl)phenyl]propionic acid as crystals melting at 107°–109°C.

To stirred polyphosphoric acid, prepared from 100 g. of phosphorus pentoxide and 70 ml. of phosphoric acid, 5.0 g. of 3-[o-(p-chlorobenzyl)phenyl]propionic acid is added. The mixture is stirred at 110°–120°C for 2 hours. Upon addition of ice-water, yellow crystals separate out. These crystals are collected by filtration, washed with water and dried. The crystals are purified by column chromatography (silica gel; eluted with a 40 : 1 mixture of benzene and ethyl acetate. The described procedure gives 4-(p-chlorobenzyl)indan-1-one as crystals melting at 87°–88°C.

REFERENCE EXAMPLES 8–10

By a similar manner to Reference example 7, the following compounds are produced.

| Reference example | Produced-compound | Starting compound |
|---|---|---|
| 8 | 4-benzylindan-1-one melting point: 71–73°C [n-hexane] | o-benzylbenzoic acid |
| 9 | 4-(p-methylbenzyl)-indan-1-one melting point: 102–105°C [cyclohexane] | o-(p-methylbenzyl)-benzoic acid |
| 10 | 4-(p-methoxybenzyl)-indan-1-one melting point: 82–84°C [cyclohexane] | o-(p-methoxybenzyl)-benzoic acid |

EXAMPLE 1-(1)

Five g. of o-benzoyl-β-phenylpropionic acid, 13 g. of anhydrous aluminum chloride and 1.3 g. of sodium chloride are admixed together and heated at 160°C for 1 hour. After cooling, water is added to the mixture, followed by extraction with chloroform. The extract is washed with a 5 % aqueous solution of sodium bicarbonate and water in that order and, then, dried. The solvent is distilled off under reduced pressure and the residue is dissolved in ethanol. The solution is decolorized with activated carbon and recrystallized from ethanol. The procedure yields 4-benzoylindan-1-one as crystals melting at 86°–88°C.

By a similar manner to Example 1-(1), the following compounds are produced.

| Example | produced-compound | starting compound |
|---|---|---|
| 1-(2) | 4-(p-toluoyl)indan-1- | 0-(p-toluoyl)-β- |

| Example | produced-compound | starting compound |
|---|---|---|
| | one<br>m.p. 106–108°C<br>[cyclohexane] | phenylpropionic acid<br>aluminum chloride<br>sodium chloride |
| 1-(3) | 5-benzoyl-1-tetralone<br>m.p. 72.5–73.5°C<br>[cyclohexane] | 0-benzoyl-r-phenyl-<br>butylic acid<br>aluminum chloride<br>sodium chloride |
| 1-(4) | 5-(p-toluoyl)-1-<br>tetralone<br>m.p. 86–87°C<br>[cyclohexane] | 0-(p-toluoyl)-r-<br>phenylbutylic acid<br>aluminum chloride<br>sodium chloride |

EXAMPLE 1-(5)

To 5.8 g. of o-(p-chlorobenzoyl)-β-phenylpropionic acid is added 50 ml. of thionyl chloride and the mixture is allowed to stand at room temperature overnight.

The excess thionyl chloride is distilled off under reduced pressure, and 13 g. of anhydrous aluminum chloride and 1.3 g. of sodium chloride are added to the resultant crude o-(p-chlorobenzoyl)-β-phenylpropionyl chloride. The mixture is heated at 160°C for 1 hour. After cooling, water is added, followed by extraction with chloroform. The extract is washed with a 5 % aqueous solution of sodium bicarbonate and water in the order mentioned and, then, dried.

The solvent is distilled off under reduced pressure and the residue is crystallized from a 1:1 mixture of benzene and cyclohexane. The described procedure gives 4-(p-chlorobenzoyl)indan-1-one as crystals melting at 145.5°–146°C.

EXAMPLE 1-(6)

By a similar manner to Example 1-(5), 6 g. of o-(p-chlorobenzoyl)-γ-phenylbutyric acid is converted to o-(p-chlorobenzoyl)-γ-phenylbutyryl chloride which, in turn, is reacted with 13 g. of anhydrous aluminum chloride and 1.3 g. of sodium chloride to prepare 5-(p-chlorobenzoyl)-1-tetralone. melting point: 96°–98°C (recrystallization solvent: cyclohexane).

EXAMPLE 2-(1)

To 120 ml. of ethanol is added 5.7 g. of methyl 1-oxo-indan-4-carboxylate and the mixture is stirred at room temperature.

Then, 600 mg. of sodium borohydride is added and, after stirring for 90 minutes, 4 ml. of acetone is added. The mixture is further stirred for 30 minutes, after which the solvent is distilled off under reduced pressure.

To the residue are added water and dilute hydrochloric acid, followed by extraction with ether. The extract is washed with water and a saturated aqueous solution of sodium chloride and, then, dried. Finally the solvent is distilled off under reduced pressure, whereupon methyl 1-hydroxyindan-4-carboxylate is obtained. Recrystallization from ether-petroleum ether gives crystals melting at 65°–67°C.

EXAMPLES 2-(2) – 2-(3)

In 100 ml. of water is dissolved 4.4 g. of sodium hydroxide, followed by the addition of 17.6 g. of 1-oxoindan-4-carboxylic acid.

While the mixture is cooled in an ice-water bath, 1.89 g. of sodium borohydride is added. The bath is removed and the mixture is stirred for 3 hours, after which 5 ml. of acetone is added. After 1 hour, the reaction mixture is added to a solution of 70 g. of ice and 30 ml. of concentrated hydrochloric acid and the resultant crystals are collected by filtration and recrystallized from acetone. The procedure gives 1-hydroxyindan-4-carboxylic acid melting at 174°–176°C (decomp.).

By a similar manner to the above, 1-hydroxy-1,2,3,4-tetrahydro-5-naphthoic acid is obtained from 19 g. of 1,2,3,4-tetrahydro-1-oxo-naphthoic acid and 1.89 g. of sodium borohydride. melting point: 160.5°–162.5°C (acetone).

EXAMPLE 2-(4)

To 200 ml. of ethanol is added 10.9 g. of ethyl 1,2,3,4-tetrahydro-1-oxo-5-naphthoate and while the solution is stirred at room temperature, 950 mg. of sodium borohydride is added. The mixture is stirred for 4 hours, after which 2 ml. of acetone is added. The mixture is further stirred for 30 minutes and, then, the solvent is distilled off under reduced pressure. Following the addition of 30 ml. of 2N hydrochloric acid, the residue is extracted with ethyl ether. The organic layer is washed with water and dried over anhydrous magnesium sulfate. The solvent is then distilled off under reduced pressure and the oily residue is purified by column chromatography on silica gel(100 g. silica gel; eluted with chloroform). The described procedure gives ethyl 1-hydroxy-1,2,3,4-tetrahydro-5-naphthoate as an oily product.

Infrared absorption spectrum (neat).

1715 cm$^{-1}$ (carbony of ester).

Nuclear magnetic resonance spectrum (CDCl$_3$, 100 MHz).

δ : 1.36(3H, t, —CH$_3$), 4.31(2H, q, O—CH$_2$—)
4.74(1H, t, C$_1$—H).

EXAMPLE 3-(1)

To 30 ml. of benzene is added 5.35 g. of 1-hydroxyindan-4-carboxylic acid. Following the addition of 15 ml. of thionyl chloride, the mixture is stirred fo 3 hours. Then, the reaction mixture is concentrated to dryness under reduced pressure and the resultant crystals are recrystallized from benzene. The described procedure gives 1-chloroindan-4-carboxylic acid melting at 135.5°–137.5°C.

EXAMPLE 3-(2)

In 6 ml. of chllroform is dissolved 5.7 g. of methyl 1-hydroxyindan-4-carboxylate and, under cooling with ice, the solution is stirred. Then, 3 ml. of thionyl chloride is added dropwise and, after the dropwise addition has been completed, the mixture is further stirred under cooling with ice for one hour. Then, the solvent and the excess thionyl chloride are distilled off under reduced pressure. The residue obtained is purified by column chromatography on silica gel (500 g. silica gel; eluant: chloroform). The procedure gives methyl 1-chloroindan-4-carboxylate as an oily product.

Infrared absorption spectrum (neat).

1720 cm$^{-1}$ (carbonyl of ester).

Nuclear magnetic resonance spectrum CDCl$_3$, 60 MHz).

δ : 3.9 (3H, s, —CH$_3$), 5.41(1H, t, C$_1$—H).

EXAMPLE 3-(3)

By a similar manner to Example 3-(2), ethyl 1-chloro-1,2,3,4-tetrahydro-5-naphthoate is produced from ethyl 1-hydroxy-1,2,3,4-tetrahydronaphthoate and thionyl chloride.
Infrared absorption spectrum (neat).
1720 cm$^{-1}$ (carbonyl of ester).
Nuclear magnetic resonance spectrum(CDCl$_3$, 100 MHz).
δ : 1.36(3H, t—CH$_3$), 4.31(2H, q, O—CH$_2$—), 5.29(1H, t, C$_1$—H).

EXAMPLE 4-(1)

In 15 ml. of dimethylformamide is dissolved 1.97 g. of 1-chloroindan-4-carboxylic acid, followed by the addition of 1.47 g. of sodium cyanide. The mixture is stirred for 5 hours, after which 150 ml. of water and 10 ml. of concentrated hydrochloric acid are added. The resultant crystals are collected by filtration and recrystallized from benzene. The described procedure gives 1-cyanoindan-4-carboxylic acid, melting point: 206°–208°C.

EXAMPLE 4-(2)

In 80 ml. of dimethylsulfoxide is dissolved 15 g. of methyl 1-chloroindan-4-carboxylate and the solution is stirred. The, 5.3 g. of sodium cyanide is added, followed by stirring for 8 hours. Following the addition of 750 ml. of water, the reaction mixture is extracted with ether. The extract is washed with a saturated aqueous solution of sodium chloride and, then, dried. The solvent is distilled off under reduced pressure and the residue is purified by column chromatography on silica gel (500 g. silica gel; eluant: chloroform). The described procedure gives methyl 1-cyanoindan-4-carboxylate as crystals melting at 76.5°–77.5°C.

EXAMPLE 4-(3)

In a mixture of 50 ml. of methanol and 50 ml. of water is dissolved 2.0 g. of sodium hydroxide, and 6.0 g. of methyl 1-cyanoindan-4-carboxylate is added to the resultant solution. The mixture is heated in a water bath maintained at about 50°C for about 20 minutes, after which time it is cooled, followed by the addition of 60 ml. of 1N hydrochloric acid. The resultant precipitate is extracted with chloroform and the extract is washed with water and dried. Then, the solvent is distilled off under reduced pressure, whereupon 1-cyanoindan-4-carboxylic acid is obtained as crystals melting at 206°–208°C.

EXAMPLE 4-(4)

In 44 ml. of dimethylsulfoxide is dissolved 4.4 g. of ethyl 1-chloro-1,2,3,4-tetrahydro-5-naphthoate, followed by the addition of 2 g. of sodium cyanide. The mixture is stirred at 50°C for 3 hours and following the addition of 450 ml. of 0.2N hydrochloric acid, the mixture is extracted with ethyl ether. The organic layer is washed with water and dried over anhydrous magnesium sulfate. The solvent is distilled off under reduced pressure and the resultant oily residue is purified by column chromatography on silica gel (100 g. silica gel; eluted with benzene). The procedure gives ethyl 1-cyano-1,2,3,4-tetrahydro-5-naphthoate as an oily product.
Infrared absorption spectrum (neat).
1720 cm$^{-1}$ (ester carbonyl).
2240 cm$^{-1}$ (nitrile).
Nuclear magnetic resonance spectrum (in CDCl$_3$, 100 MHz).
δ : 1.36(3H, t, —CH$_3$), 4.00(1H, t, C$_1$—H), 4.33(2H, q, O—CH$_2$—).

EXAMPLE 4-(5)

In 90 ml. of ethanol is dissolved 9.6 g. of ethyl 1-cyano-1,2,3,4-tetrahydro-5-naphthoate and a solution of 2.5 g. of sodium hydroxide in 90 ml. of water is added. The mixture is stirred under heating at 50°C for 3 hours, after which the ethanol is distilled off. Then, following the addition of 2N hydrochloric acid, the residue is extracted with chloroform. The organic layer is washed with water and dried over anhydrous magnesium sulfate. The solvent is distilled off under reduced pressure and the crystalline residue is recrystallized from benzene. The described procedure gives 1-cyano-1,2,3,4-tetrahydro-5-naphthoic acid, melting point: 177°–179°C.

EXAMPLE 5-(1)

To 40 ml. of pyridine is added 19.2 g. of methyl 1-hydroxyindan-4-carboxylate and, while the mixture is stirred at a temperature of not more than 10°C, 21 g. of p-toluenesulfonyl chloride is added in small installments. After the addition has been completed, the reaction mixture is allowed to stand at a temperature not exceeding 10°C for 6 hours. Then, following the addition of ice, the reaction mixture is extracted with ether. The extract is washed with water and dried. The solvent is then distilled off under reduced pressure and the resultant 4-carbomethoxy-1-indanyl p-toluenesulfonate is dissolved in 100 ml. of dimethylsulfoxide, followed by stirring. Then, 5.5 g. of sodium cyanide is added and the mixture is stirred at room temperature for 11 hours. Following the addition of 850 ml. of water, the reaction mixture is extracted with ether. The extract is washed with a saturated aqueous solution of sodium chloride and, then, dried. The solvent is distilled off under reduced pressure and the residue is purified by column chromatography on silica gel (600 g. silica gel; eluant: chloroform). The described procedure gives methyl 1-cyanoindan-4-carboxylate as crystals melting at 76°–77°C.

EXAMPLE 5-(2)

To 100 ml. of benzene is added 19.2 g. of 1-hydroxy-1,2,3,4,-tetrahydro-5-naphthoic acid, and following the addition of 50 ml. of thionyl chloride, the solution is stirred for 8 hours. The solvent and the excess thionyl chloride are distilled off under reduced pressure and, then, 150 ml. of dimethylsulfoxide and 19.6 g. of sodium cyanide are added, followed by stirring at 50°C for 6 hours. Then, it is added to 1.5 l. of 1N hydrochloric acid and extracted with ethyl ether. The organic layer is extracted with 800 ml. of 5 % aqueous sodium hydroxide solution and after the addition of 100 ml. of concentrated hydrochloric acid, the solution is extracted with chloroform. The chloroform layer is washed with water and dried over anhydrous magnesium sulfate. The solvent is distilled off under reduced pressure and the crystalline residue is recrystallized from benzene. The procedure gives 1-cyano-1,2,3,4-tetrahydro-5-naphthoic acid, melting point: 177°–179°C.

EXAMPLE 6-(1)

To dilute sulfuric acid, prepared from 54 ml. of water and 45 ml. of concentrated sulfuric acid, there is added 3 g. of 4-benzoylindan-1-carbonitrile. The mixture is refluxed in a current of nitrogen gas for three hours and a half. After cooling, the reaction mixture is diluted with water and extracted with ether. The ethereal layer is further extracted with a 5 % aqueous solution of potassium carbonate and the extract is washed with ether and rendered acidic with hydrochloric acid. The precipitate is extracted with chloroform and the extract is washed with water and dried. The solvent is distilled off under reduced pressure, whereupon 4-benzoylindan-1-carboxylic acid is obtained. Recrystallization from benzene-cyclohexane (7:20) gives crystals melting at 100°–102°C.

EXAMPLE 6-(2)

To dilute sulfuric acid, prepared from 27 ml. of water and 23 ml. of concentrated sulfuric acid, there is added 3 g. of 4-(p-toluoyl)indan-1-carbonitrile. The mixture is refluxed in a current of nitrogen gas for 3.5 hours. After cooling, the reaction mixture is diluted with water and extracted with ether. The ethereal layer is extracted with a 5 % aqueous solution of potassium carbonate and the extract is washed with water and rendered acidic with hydrochloric acid. The precipitate is extracted with chloroform and the extract is washed with a saturated aqueous solution of sodium chloride and dried. The solvent is then distilled off under reduced pressure and the residue is crystallized from benzene-cyclohexane (7:20). The described procedure gives 4-p-toluoylindan-1-carboxylic acid as crystals melting at 128°–131°C.

EXAMPLE 6-(3)

In 500 ml. of methanol is dissolved 15 g. of 4-benzoylindan-1-carbonitrile, followed by the addition of 150 ml. of a 5 % aqueous solution of sodium hydroxide and 50 ml. of a 30 % aqueous solution of hydrogen peroxide.

The mixture is heated at 60°C for 2 hours and cooled. The reaction mixture is rendered acidic by the addition of dilute hydrochloric acid and the resultant precipitate is extracted with ethyl acetate.

The extract is washed with water and dried. The solvent is distilled off under reduced pressure and the residue is purified by column chromatography on silica gel ([500 g. silica gel; eluted with chloroform-acetone (7:3)]. The described procedure gives 4-benzoylindan-1-carboxamide as crystals melting at 164.5°–166°C.

EXAMPLES 6-(4) – 6-(11)

By a similar manner to Example 6-(1), following compounds are produced.

| Example | Produced-compound | Starting compound |
|---|---|---|
| 6-(4) | 4-(p-chlorobenzoyl)-indan-1-carboxylic acid melting point: 138.5–139.5°C [benzene-cyclohexane (3:10)] | 4-(p-chlorobenzoyl)-indan-1-carbonitrile |
| 6-(5) | 4-(p-bromobenzoyl)-indan-1-carboxylic acid melting point: 147.0–149.0°C [benzene-cyclohexane (1:1)] | 4-(p-bromobenzoyl)-indan-1-carbonitrile |
| 6-(6) | 4-(p-chloro-m-methylbenzoyl)indan-1-carboxylic acid melting point: 116–117°C [benzene-cyclohexane(3:20)] | 4-(p-chloro-m-methylbenzoyl)indan-1-carbonitrile |
| 6-(7) | 4-(p-t-butylbenzoyl)-indan-1-carboxylic acid melting point: 139–142°C [benzene-petroleum ether] | 4-(p-t-butylbenzoyl)-indan-1-carbonitrile |
| 6-(8) | 4-(p-fluorobenzoyl)-indan-1-carboxylic acid melting point: 109–110°C [benzene-cyclohexane (3:20)] | 4-(p-fluorobenzoyl)-indan-1-carbonitrile |
| 6-(9) | 5-benzoyl-1,2,3,4-tetrahydro-1-naphthoic acid melting point: 164–165°C [benzene] | 5-benzoyl-1,2,3,4-tetrahydro-1-naphthonitrile |
| 6-(10) | 5-(p-toluoyl)-1,2,3,4-tetrahydro-1-naphthoic acid melting point: 102–103°C [cyclohexane] | 5-(p-toluoyl)-1,2,3,4-tetrahydro-1-naphthonitrile |
| 6-(11) | 5-(p-chlorobenzoyl)-1,2,3,4-tetrahydro-1-naphthoic acid melting point: 152.5–153°C [benzene-hexane] | 5-(p-chlorobenzoyl)-1,2,3,4-tetrahydro-1-naphthonitrile |

EXAMPLES 6-(12) – 6-(15)

By a similar manner to Example 6-(3), following compounds are produced.

| Example | Produced-compound | Starting compound |
|---|---|---|
| 6-(12) | 5-benzoyl-1,2,3,4-tetrahydro-1-naphthamide melting point: 145.5–147.5°C [cyclohexane] | 5-benzoyl-1,2,3,4-tetrahydro-1-naphthonitrile |
| 6-(13) | 5-(p-toluoyl)-1,2,3,4-tetrahydro-1-naphthamide melting point: 178–178.5°C [ethanol] | 5-(p-toluoyl)-1,2,3,4-tetrahydro-1-naphthonitrile |
| 6-(14) | 5-(p-chlorobenzoyl)-1,2,3,4-tetrahydro-1-naphthamide melting point: 150.5–152.5°C (benzene) | 5-(p-chlorobenzoyl)-1,2,3,4-tetrahydro-1-naphthonitrile |
| 6-(15) | 4-(2,4,6-trimethylbenzoyl)indan-1-carboxamide melting point: 195–198°C [ethanol] | 4-(2,4,6-trimethylbenzoyl)indan-1-carbonitrile |

EXAMPLE 6-(16)

To 100 g. of polyphosphoric acid is added 2 g. of 4-(p-chlorobenzoyl)indan-1-carbonitrile and the mixture is heated at 150°–170°C for 2 hours.

The mixture is allowed to stand at room temperature overnight and following the addition of water, it is extracted with ethyl acetate. The extract is washed with 5 % aqueous sodium bicarbonate and water in that order and, then, dried over sodium sulfate.

The solvent is distilled off under reduced pressure and the solid residue is recrystallized from 80 ml. of benzene. The procedure gives 4-(p-chlorobenzoyl)indan-1-carboxamide as colorless crystals melting at 159°–161°C. The crystal includes 1/6 mole equivalent of benzene.

EXAMPLE 6-(17)

To 2.3 g. of 4-(p-toluoyl)indan-1-carbonitrile is added 75 g. of polyphosphoric acid and the mixture is worked into a homogeneous solution by heating on a water bath at 90°C for 30 minutes and, then, on an oil bath at 120°–130°C for 30 minutes. Following the addition of water to decompose the polyphosphoric acid, the reaction mixture is extracted with ethyl acetate. The extract is washed with water, 5 % aqueous sodium hydrogen carbonate and water in the order mentioned and, then, dried. It is, then, treated with activated carbon and concentrated under reduced pressure. The resultant crystalline residue is recrystallized from a mixture of ethanol and ethyl acetate. The described procedure gives 4-(p-toluoyl)indan-1-carboxamide as crystals melting at 188°–191°C.

EXAMPLE 6-(18)

To 3.0 g. of 4-(p-methoxybenzoyl)indan-1-carbonitrile is added 150 g. of polyphosphoric acid and the mixture is homogenized by heating in an oil bath at about 120°C. After 40 minutes of heating, the mixture is allowed to stand at room temperature overnight. The polyphosphoric acid is decomposed with 200 ml. of water, followed by extraction with ethyl acetate. The extract is washed with water and dried. The solvent is then distilled off under reduced pressure and the residue is recrystallized from benzene. The described procedure gives 4-(p-methoxybenzoyl)indan-1-carboxamide as crystals melting at 164°–166°C.

EXAMPLE 6-(19)

In 1 l. of a 10 % aqueous solution of hydrogen peroxide is dissolved 8 g. of sodium hydroxide and, then, 20.1 g. of 1-cyano-1,2,3,4-tetrahydro-5-naphthoic acid is added.

The mixture is stirred at 50°C for 20 hours, after which time 250 ml. of 1N hydrochloric acid is added. The resultant crystals are collected by filtration, washed with water and recrystallized from ethanol. The procedure gives 1-carbamoyl-1,2,3,4-tetrahydro-5-naphthoic acid, melting point: 247°–249°C.

EXAMPLE 6-(20)

To 500 g. of polyphosphoric acid is added 22.4 g. of ethyl 1-cyano-1,2,3,4-tetrahydro-5-naphthoate and the mixture is stirred at 90°–100°C for 2 hours. Then, 1 l. of water is added, followed by cooling. The resultant crystals are collected by filtration, washed with water and recrystallized from ethanol. The procedure gives ethyl 1-carbamoyl-1,2,3,4-tetrahydro-5-naphthoate, melting point: 159.5°–161.5°C.

EXAMPLE 6-(21)

To 60 ml. of 60% sulfuric acid is added 3.0 g. of 4-(p-chlorobenzyl)indan-1-carbonitrile and the mixture is refluxed in a current of nitrogen gas for 2 hours. After cooling, water is added and the mixture is extracted with ether. The ethereal solution is washed with water and extracted with a 5 % aqueous solution of potassium carbonate. The extract is rendered acidic with hydrochloric acid and the resultant precipitate is extracted with chloroform. The chloroform layer is washed with water and dried. The solvent is distilled off under reduced pressure and the residue is crystallized from cyclohexane. The described procedure gives 4-(p-chlorobenzyl)indan-1-carboxylic acid as crystals melting at 127°–129°C.

EXAMPLE 6-(22) – 6-(24)

By a similar manner to Example 6-(21), the following compounds are produced.

| Example | Produced-compound | Starting compound |
| --- | --- | --- |
| 6-(22) | 4-benzylindan-1-carboxylic acid melting point: 119.5–121°C [cyclohexane] | 4-benzylindan-1-carbonitrile |
| 6-(23) | 4-(p-methylbenzyl)-indan-1-carboxylic acid melting point: 124.5–126.5°C [cyclohexane] | 4-(p-methylbenzyl)-indan-1-carbonitrile |
| 6-(24) | 4-(p-methoxybenzyl)-indan-1-carboxylic acid melting point: 109.5–111.5°C [cyclohexane] | 4-(p-methoxybenzyl)-indan-1-carbonitrile |

EXAMPLE 7-(1)

In 100 ml. of dry tetrahydrofuran is dissolved 3.6 g. of 1,3-dithian and while the solution is chilled to −30°C in nitrogen gas streams and stirred, 10 ml. of a 20 % solution of n-butyl lithium in hexane is added dropwise over a period of about 15 minutes. After the dropwise addition has been completed, the solution is stirred at that temperature for 2 hours and, then, at −5°C for 30 minutes. The solution is chilled again to −20°C and, under stirring, a solution of 7.1 g. of 4-benzoylindan-1-one in 75 ml. of dry tetrahydrofuran is added dropwise. After the dropwise addition has been completed, the mixture is stirred at that temperature for 1 hour, after which it is allowed to stand at 0°C overnight. Then, the solvent is distilled off undr reduced pressure. To the residue is added 15 ml. of dilute hydrochloric acid, followed by extraction with ether. The extract is washed with water and aqueous sodium chloride and, then, dried. The solvent is distilled off under reduced pressure and the residue is purified by column chromatography on silica gel (500 g. silica gel, eluted with a 20:1 mixture of benzene and ethyl acetate). The described procedure gives 2-(4-benzoyl-1-hydroxy-1-indanyl)-1,3-dithian as an oily product. The infrared absorption spectrum (neat) of this product is in good agreement with the assumed structure, absorbing at 1660 cm$^{-1}$(ketone) and 3450 cm$^{-1}$(hydroxyl).

EXAMPLE 8-(1)

In 300 ml. of benzene is dissolved 1.4 g. of 2-(4-benzoyl-1-hydroxy-1-indanyl)-1,3-dithian, followed by the addition of 600 mg. of p-toluenesulfonic acid. The mixture is refluxed for 3 hours with removing the water azeotropically. After cooling, the solution is washed with water, aqueous sodium bicarbonate and water in the order mentioned and dried. The solvent is distilled off under reduced pressure, whereupon 2-(4-benzoyl-1-indanylidene)-1,3-dithian is obtained as an oily product. This product is used in the following reaction without purification.

EXAMPLE 9-(1)

To 0.8 g. of 2-(4-benzoyl-1-indanylidene)-1,3-dithian are added 150 ml. of glacial acetic acid and 50 ml. of concentrated hydrochloric acid and the mixture is refluxed for 3 hours, after which the solvent is distilled off under reduced pressure. The residue is extracted with ether.

The ethereal layer is washed with water and extracted with 5 % aqueous sodium carbonate. The extract is washed with ether and rendered acidic with hydrochloric acid. The oily precipitate is extracted with ether. The extract is washed with water and aqueous solution of sodium chloride, and dried. The solvent is distilled off under reduced pressure and the residue is crystallized from benzene-cyclohexane. The described procedure gives 4-benzoylidan-1-carboxylic acid as crystals melting at 100°–102°C.

EXAMPLE 9-(2)

In 200 ml. of ethanol is dissolved 2.0 g. of the 2-(4-benzoyl-1-indanylidene)-1,3-dithian obtained by the procedure of Example 8-(1), and the solution is cooled with ice. Hydrogen chloride gas is bubbled through the solution for 15 minutes, after which it is allowed to stand under cooling with ice for 2 hours and, then, at room teperature overnight. The excess hydrogen chloride and solvent are distilled off under reduced pressure and, following the addition of water, the residue is extracted with ether. The extract is washed with water and dried. The solvent is distilled off under reduced pressure and the residue is purified by column chromatography on slica gel (200 g. silica gel; eluted with a 2.5 % solution of ethyl acetate in benzene). The described procedure gives ethyl 4-benzoylindan-1-carboxylate as an oil.

Infrared absorption spectrum (neat)
1720 cm$^{-1}$ (ester carbonyl)
1650 cm$^{-1}$ (ketone carbonyl)

EXAMPLE 10-(1)

In 100 ml. of dry tetrahydrofuran is dissolved 3.6 g. of 1,3-dithian and, under cooling at −30°C and stirring in a current of nitrogen gas, 10 ml. of a 20 % solution of n-butyl lithium in hexane is added dropwise over a period of about 20 minutes. After the dropwise addition has been completed, the mixture is stirred at the temperature mentioned for 2 hours and, then, at −5°C for 30 minutes. The solution is chilled again to −20°C and, under stirring, a solution of 8.1 g. of 4-(p-chlorobenzoyl)indan-1-one in 75 ml. of dry tetrahydrofuran is added dropwise. After the drop-by-drop addition has been completed, the mixture is stirred at the temperature mentioned for 1 hour and, then, allowed to stand at 0°C overnight. Then, the solvent is removed by distillation under reduced pressure. Dilute hydrochloric acid is added to the residue and the mixture is extracted with ether. The extract is washed with water and aqueous solution of sodium chloride and, then, dried. The solvent is distilled off under reduced pressure and the residue is subjected, without being purified, to the dehydration reaction. Thus, the residue is dissolved in 350 ml. of benzene, and 600 mg. of p-toluenesulfonic acid is added. The solution is refluxed for 3 hours with removing the water azeotropically. After cooling, the solution is washed with water, aqueous sodium bicarbonate and water in the order mentioned. The solvent is distilled off under reduced pressure and the residue is hydrolyzed, without a purification procedure. Thus, to the residue are added 150 ml. of glacial acetic acid and 50 ml. of concentrated hydrochloric acid and the mixture is refluxed for 3 hours, after which the solvent is distilled off under reduced pressure. The residue is diluted with water and extracted with ether. The ethereal layer is washed with water and extracted with a 5 % aqueous solution of sodium carbonate. The extract is washed with ether and rendered acidic with hydrochloric acid. The resultant precipitate is extracted with chloroform and the extract is washed with water and dried. The solvent is distilled off under reduced pressure and the residue is crystallized from benzene-cyclohexane (3:10). The foregoing procedure gives 4-(p-chlorobenzoyl)indan-1-carboxylic acid as crystals melting at 137°–139°C.

EXAMPLES 10-(2) – 10-(7)

By a similar manner to Example 10-(1), following compounds is produced.

| Example | Produced-compound | Starting compound |
|---|---|---|
| 10-(2) | 4-(p-methylbenzoyl)-indan-1-carboxylic acid<br>melting point: 129.5–131.0°C<br>[benzene-cyclohexane (8:25)] | 1,3-dithian n-butyl lithium 4-(p-methylbenzoyl)indan-1-one |
| 10-(3) | 4-(p-chloro-m-methylbenzoyl)indan-1-carboxylic acid<br>melting point: 115.0–116.5°C<br>[benzene-cyclohexane (3:20)] | 1,3-dithian n-butyl lithium 4-(p-chloro-m-methylbenzoyl)-indan-1-one |
| 10-(4) | 5-benzoyl-1,2,3,4-tetrahydro-1-naphthoic acid<br>melting point: 164–165°C [benzene] | 1,3-dithian n-butyl lithium 5-benzoyl-1-tetralone |
| 10-(5) | 5-(p-methylbenzoyl)-1,2,3,4-tetrahydro-1-naphthoic acid<br>melting point: 102–103°C<br>[cyclohexane] | 1,3-dithian n-butyl lithium 5-(p-methylbenzoyl)-1-tetralone |
| 10-(6) | 5-(p-chlorobenzoyl)-1,2,3,4-tetrahydro-1-naphthoic acid<br>melting point: 152.5–153.5°C<br>[benzene-hexane] | 1,3-dithian n-butyl lithium 5-(p-chlorobenzoyl)-1-tetralone |
| 10-(7) | indan-1,4-dicarboxylic acid<br>melting point: 245.5–248°C<br>[acetone] | 1,3-dithian n-butyl lithium methyl 1-oxoindan-4-carboxylate |

EXAMPLE 11-(1)

To 100 ml. of dry benzene are added 17.6 g. of 1-oxoindan-4-carboxylic acid and 22.9 g. of phosphorus pentachloride and, after stirring for 1.5 hours, 40 g. of aluminum chloride is added. The mixture is stirred for 5 hours, after which the product is poured into dilute hydrochloric acid and extracted with ether. The organic layer is dried and distilled free of the solvent under reduced pressure. The crystalline residue is recrystallized from cyclohexane. The described procedure gives 4-benzoylindam-1-one which melts at 87°–89°C.

EXAMPLE 11-(2)

To 100 ml. of dry toluene are added 17.6 g. of 1-oxoindan-4-carboxylic acid and 22.9 g. of phosphorus pentachloride. The mixture is stirred at room temperature for 1.5 hours, after which time 40 g. of aluminum chloride is added. The mixture is stirred overnight and, then, poured into 400 ml. of 3N hydrochloric acid, followed by extraction with benzene. The organic layer is washed with water, aqueous sodium hydroxide and water in the order mentioned and dried with anhydrous magnesium sulfate. The solvent is distilled off under reduced pressure and the resultant crystalline residue is purified by column chromatography on silica gel (200 g. silica gel; eluted with chloroform).

Finally, the eluate is recrystallized from acetone to give 4-(p-toluoyl)indan-1-one, melting point: 105°–108°C.

EXAMPLES 11-(3) – 11-(5)

By a similar manner to Example 11-(2), the following compounds are produced.

| Example | Produced-compound | Starting compound |
|---|---|---|
| 11-(3) | 4-(2,4,6-trimethyl-benzoyl)indan-1-one melting point: 159.5–161.5°C [benzene-hexane (1:1)] | 1-oxoindan-4-carboxylic acid mesitylene |
| 11-(4) | 5-benzoyl-3,4-dihydro-1(2H)-naphthalenone melting point: 72.5–73.5°C [cyclohexane] | 1,2,3,4-tetrahydro-1-oxo-5-naphthoic acid benzene |
| 11-(5) | 5-(p-chlorobenzoyl)-3,4-dihydro-1(2H)-naphthalenone melting point: 96–98°C [cyclohexane] | 1,2,3,4-tetrahydro-1-oxo-5-naphthoic acid p-chlorobenzene |

EXAMPLE 11-(6)

To 200 ml. of chlorobenzene are added 17.6 g. of 1-oxoindan-4-carboxylic acid and 23 g. of phosphorus pentachloride. The mixture is stirred at room temperature for 3 hours, after which time 40 g. of aluminum chloride is added. The mixture is stirred at about 65°C for 3 hours. After cooling, the mixture is poured into ice and hydrochloric acid, followed by extraction with chloroform. The extract is washed with water, a saturated aqueous solution of sodium bicarbonate and water in the order mentioned. After drying, the solvent is distilled off under reduced pressure and the residue is purified by column chromatography on silica gel (200 g. silica gel; eluted with chloroform). Finally, recrystallization from a 20:5 mixture of benzene and hexane gives 4-(p-chlorobenzoyl)indan-1-one as crystals melting at 144.5°–146°C.

EXAMPLES 11-(7) – 11-(10)

By a similar manner to Example 11-(6), the following compounds are produced.

| Example | Produced-compound | Starting compound |
|---|---|---|
| 11-(7) | 4-(p-chloro-m-methyl-benzoyl)indan-1-one melting point: 88–90°C [benzene-cyclohexane(3:20)] | 1-oxoindan-4-carboxylic acid orthochlorotoluene |
| 11-(8) | 4-(p-fluorobenzoyl)indan-1-one melting point: 93–94°C | 1-oxoindan-4-carboxylic acid fluorobenzene |
| 11-(9) | [chloroform] 4-(p-bromobenzoyl)-indan-1-one melting point: 154–155°C [benzene-cyclohexane (1:1)] | 1-oxoindan-4-carboxylic acid bromobenzene |
| 11-(10) | 5-(p-toluoyl)-3,4-dihydro-1(2H)-naphthalenone melting point: 86–87°C [cyclohexane] | 1,2,3,4-tetrahydro-1-oxo-5-naphthoic acid phosphorus pentachloride toluene |

EXAMPLE 11-(11)

To 5.5 g. of 1-cyanoindan-4-carboxylic acid is added 80 ml. of thionyl chloride, and the mixture is allowed to stand at room temperature for 15 hours. Then, the excess thionyl chloride is removed under reduced pressure. To the resultant 1-cyanoindan-4-carbonyl chloride are added. 50 ml. of dry benzene and 8.0 g. of anhydrous aluminum chloride powder and the mixture is heated at about 60°C for 40 minutes. After cooling, the mixture is poured into ice-hydrochloric acid, followed by extraction with ether. The extract is washed with 1N hydrochloric acid and a saturated aqueous solution of sodium chloride and, then, dried. The solvent is distilled off under reduced pressure and the residue is purified by column chromatography on silica gel (400 g. of silica gel; eluted with chloroform).

The described procedure gives 4-benzoylindan-1-carbonitrile as an oily product.

Infrared absorption spectrum (neat).
1660 $cm^{-1}$ (carbonyl).
2230 $cm^{-1}$ (nitrile).
Nuclear magnetic resonance spectrum ($CDCl_3$, 60 MHz).
$\delta$ : 4.26 (1H, t, $C_1$—H).

EXAMPLE 11-(12)

To 6.0 g. of 1-cyanoindan-4-carboxylic acid is added 96 ml. of thionyl chloride and the mixture is allowed to stand at room temperature for 15 hours. The excess thionyl chloride is removed under reduced pressure. To 1-cyanoindan-4-carbonyl chloride, which is thus obtained as the residue, are added 50 ml. of anisole, 50 ml. of methylene chloride and 6.0 g. of anhydrous aluminum chloride powder. The mixture is stirred at room temperature for 90 minutes. After cooling, the product is poured into ice-hydrochloric acid and extracted with ether. The extract is washed with 1N hydrochloric acid and a saturated aqueous solution of sodium chloride, followed by drying. The solvent is distilled under reduced pressure and the residue obtained is purified by chromatography on a column of silica gel (700 g. silica gel; eluted with chloroform). The procedure gives 4-(p-methoxybenzoyl)indan-1-carbonitrile as crystals melting at 109°–112°C.

EXAMPLE 11-(13)

To 6.0 g. of 1-cyanoindan-4-carboxylic acid is added 96 ml. of thionyl chloride and the mixture is allowed to stand at room temperature for 14 hours. The excess thionyl chloride is removed under reduced pressure. To 1-cyanoindan-4-carbonylchloride, which is thus obtained as the residue, are added 50 ml. of toluene and 50 ml. of methylene chloride, followed by the addition of 6.0 g. of anhydrous aluminum chloride. The mixture is stirred at room temperature for 1 hour. After cooling, the reaction product is poured into ice-hydrochloric acid and extracted with ether. The extract is washed with 1N hydrochloric acid and a saturated aqueous solution of sodium chloride, followed by drying. The solvent is distilled off under reduced pressure and the residue is purified by column chromatograhy on silica gel (500 g. silica gel; eluted with chloroform). The procedure gives 4-(p-toluoyl)indan-1-carbonitrile as an oily product.

Infrared absorption spectrum (neat).
1655 cm$^1$ (carbonyl).
2230 cm$^{-1}$ (nitrile).
Nuclear magnetic resonance spectrum ($CDCl_3$, 6MHz).
δ : 4.2 (1H, t, $C_1$-H), 2.45(3H, s, —$CH_3$).

EXAMPLE 11-(14)

To 6.0 g. of 1-cyanoindan-4-carboxylic acid are added 20 ml. of chloroform and 80 ml. of thionyl chloride and the mixture is allowed to stand at room temperature for 15 hours. The excess thionyl chloride and chloroform are distilled off under reduced pressure. To 1-cyanoindan-4-carbonyl chloride, which is thus obtained as the distillation residue, is added 100 ml. of chlorobenzene, followed by stirring under cooling with ice. Then, 6.0 g. of anhydrous aluminum chloride powder is added and the temperature is gradually increased to about 80°C, at which temperature the reaction mixture is stirred for 2.5 hours. After cooling, ice-hydrochloric acid is added, followed by extraction with ether. The extract is washed with water and dried. Then, the solvent is distilled off under reduced pressure and the residue obtained is purified by column chromatography on silica gel (700 g. silica gel; eluant: chloroform). The described procedure gives 4-(p-chlorobenzoyl)indan-1-carbonitrile as an oily product.

Infrared absorption spectrum (neat)
1660 cm$^{-1}$ (carbonyl)
2230 cm$^{-1}$ (nitrile)
Nuclear magnetic resonance spectrum ($CDCl_3$, 60 MHz)
δ : 4.17 (1H, t, $C_1$—H)

EXAMPLES 11-(15) – 11-(17)

By a similar manner to Example 11-(11) the following compounds are produced.

EXAMPLE 11-(18)

To 4.0 g. of 1-cyanoindan-4-carboxylic acid are added 60 ml. of chloroform and 60 ml. of thionyl chloride and the mixture is allowed to stand at room temperature for 2 days.

The excess thionyl chloride and the chloroform are distilled off under reduced pressure and 30 g. of t-butylbenzene added to the resultant acid chloride. Then, under cooling with ice and stirring, 10 g. of aluminum chloride is added. The mixture is stirred at room temperature for 30 minutes, at 50°C for another 30 minutes and, then, at room temperature for 3 hours.

Ice is added to the reaction mixture, followed by extraction with benzene. The extract is washed with water and dried. Then, the solvent is distilled off under reduced pressure and the residue is purified by column chromatography (600 g. silica gel; eluted with a 100:0.5 mixture of benzene and ethyl acetate). The described procedure gives 1-cyano-4-(p-t-butylbenzoyl)indan.

Infrared absorption spectrum (neat)
2250 cm$^{-1}$ (nitrile)
1660 cm$^{-1}$ (ketone)

EXAMPLE 11-(19)

To 130 ml. of thionyl chloride is added 10.2 g. of 1-carbamoylindan-4-carboxylic acid and the mixture is allowed to stand at room temperature for 14 hours.

The excess thionyl chloride is distilled off under reduced pressure. To the 1-carbamoylindan-4-carbonyl chloride obtained as the distillation residue are added 50 ml. of benzene, 50 ml. of carbon disulfide and 10.0 g. of anhydrous aluminum chloride powder, and the mixture is stirred at about 40°C for 30 minutes. After cooling, ice-hydrochloric acid is added, followed by extraction with ethyl acetate. The extract is washed with 1N hydrochloric acid and a saturated aqueous solution of sodium chloride, followed by drying. The solvent is distilled off under reduced pressure and the residue is purified by column chromatography on silica gel [500 g. silica gel; eluted with chloroform-acetone (7:3)].

The described procedure gives 4-benzoylindan-1-carboxamide as crystals melting at 163.5°–165.5°C.

EXAMPLES 11-(20) – 11-(22)

By a similar manner to Example 11-(19), the following compounds are produced.

| Example | Produced-compound | Starting compound |
|---|---|---|
| 11-(15) | 5-benzoyl-1,2,3,4-tetrahydro-1-naphthonitrile melting point: 91.5–93.5°C [n-hexane] | 1-cyano-1,2,3,4-tetrahydro-5-naphthoic acid thionyl chloride benzene |
| 11-(16) | 5-(p-toluoyl)-1,2,3,4-tetrahydro-1-naphtho-nitrile melting point: 72–73°C [n-hexane] | 1-cyano-1,2,3,4-tetrahydro-5-naphthoic acid toluene |
| 11-(17) | 5-(p-chlorobenzoyl)-1,2,3,4-tetrahydro-1-naphthonitrile melting point: 97–99°C [n-hexane] | 1-cyano-1,2,3,4-tetrahydro-5-naphthoic acid thionyl chloride chlorobenzene |
| 11-(20) | 5-benzoyl-1,2,3,4-tetrahydro-1-naphthamide melting point: 145.5–147.5°C [cyclohexane] | 1-carbamoyl-1,2,3,4-tetrahydro-5-naphthoic acid benzene |
| 11-(21) | 5-(p-toluoyl)-1,2,3,4-tetrahydro-1-naphthamide melting point: 178–178.5°C [ethanol] | 1-carbamoyl-1,2,3,4-tetrahydro-5-naphthoic acid toluene |
| 11-(22) | 5-(p-chlorobenzoyl)-1,2,3,4-tetrahydro-1-naphthamide melting point: 150.5–152.5°C [benzene] | 1-carbamoyl-1,2,3,4-tetrahydro-5-naphthoic acid chlorobenzene |

EXAMPLE 12-(1)

To 120 ml. of carbon disulfide is added 54 g. of anhydrous aluminum chloride powder on an ice bath, followed by the dropwise addition of a solution of 11.4 g. of ethyl indan-1-carboxylate in 60 ml. of carbon disulfide. The mixture is stirred for 10 minutes, after which a solution of 42 g. of benzoyl chloride in 60 ml. of carbon disulfide is added dropwise. After the dropwise addition has been completed, the temperature is gradually increased and the solution is stirred on reflux for 3 hours and thirty minutes to complete the reaction. Ice and hydrochloric acid are added to the reaction mixture followed by extraction with ether. The extract is washed with 1N hydrochloric acid, water, a saturated aqueous solution of sodium bicarbonate and a saturated aqueous solution of sodium chloride in the order mentioned and, then, dried over anhydrous sodium sulfate. The solvent is then distilled off under reduced pressure and the residue is column-chromatographed on silica gel (conditions: 2 Kg. of silica gel; eluant solvent-benzene containing 2.5 % of ethyl acetate). The first-emerging fractions rich in ethyl 4-benzoylindan-1-carboxylate are pooled separate from the ensuing fractions rich in ethyl 6-benzoylindan-1-carboxylate. The former fractions are further purified by rechromatography on a column of silica gel, whereby ethyl 4-benzoyl-indan-1-carboxylate is obtained as an oily product.
Infrared absorption spectrum (neat)
1720 cm$^{-1}$ (ester carbonyl)
1650 cm$^{-1}$ (keton carbonyl)

EXAMPLES 12-(2) – 12-(5)

By a similar manner to Example 12-(1), the following compounds are produced.

| Example | Produced-compound | Starting compound |
| --- | --- | --- |
| 12-(2) | 4-(p-toluoyl)indan-1-carboxamide melting point: 188–191°C[ethanol-ethyl acetate] | indan-1-carboxamide p-toluoyl chloride |
| 12-(3) | 5-benzoyl-1,2,3,4-tetrahydro-1-naphthamide melting point: 145.5–147.5 [cyclohexane] | 1,2,3,4-tetrahydro-1-naphthamide benzoyl chloride |
| 12-(4) | 5-(p-toluoyl-1,2,3,4-tetrahydro-1-naphthamide melting point: 178–178.5°C [ethanol] | 1,2,3,4-tetrahydro-1-naphthamide p-toluoyl chloride |
| 12-(5) | 5-(p-chlorobenzoyl)-1,2,3,4-tetrahydro-1-naphthamide melting point: 150.5–152.5°C [benzene] | 1,2,3,4-tetrahydro-1-naphthamide p-chlorobenzoyl chloride |

EXAMPLE 13-(1)

In 100 ml. of acetic acid is dissolved 11.1 g. of 4-benzyl indan-1-one, followed by the addition of 13.4 g. of chromic acid and 2.5 ml. of concentrated sulfuric acid. The mixture is stirred at room temperature for 2 hours, after which it is poured into 4 l. of water. After 200 g. of anhydrous potassium carbonate is added, the mixture is extracted with chloroform. The organic layer is washed with water and dried over anhydrous magnesium sulfate. The solvent is distilled off under reduced pressure and the oily residue is purified by column chromatography on silica gel with chloroform as the eluent and, then, recrystallized from cyclohexane. The procedure gives 4-benzoylindan-1-one melting at 87°–89°C.

EXAMPLES 13-(2) – 13-(3)

By a similar manner to Example 13-(1), the following compounds are produced.

| Example | Produced-compound | Starting compound |
| --- | --- | --- |
| 13-(2) | 4-(p-chlorobenzoyl)-indan-1-one melting point: 145–146°C [benzene-cyclohexane (1:1)] | 4-(p-chlorobenzyl)-indan-1-one chromic anhydride |
| 13-(3) | 4-(p-toluoyl)indan-1-one [acetone] | 4-(p-methylbenzyl)-indan-1-one chromic anhydride |

EXAMPLE 13-(4)

To 60 ml. of dioxane are added 8.0 g. of 4-(p-methoxybenzyl)indan-1-carbonitrile and 2.8 g. of selenium dioxide and the mixture is refluxed for 12 hours. After cooling, water is added, followed by extraction with chloroform. The extract is washed with water and dried. Then, the solvent is distilled off under reduced pressure and the residue is purified by column chromatography (500 g. silica gel; eluted with chloroform). The crude crystals thus obtained are recrystallized from benzene. The procedure gives 4-(p-methoxybenzoyl)indan-1-carbonitrile as crystals melting at 115.5°–117.5°C.

EXAMPLE 13-(5)

In 100 ml. of acetic acid is dissolved 6.7 g. of 5-benzyl-1,2,3,4-tetrahydro-1-naphthoic acid and, under cooling with ice, 3.4 g. of chromic anhydride is added. The mixture is stirred well. After stirring overnight, the reaction mixture is poured over 500 g. of ice and extracted with chloroform.
The chloroform layer is washed with water and dried over anhydrous magnesium sulfate. The solvent is distilled off under reduced pressure and the residual oily liquid is chromatographed on a column of silica gel equilibrated with oxalic acid with chloroform as the eluent and, then, recrystallized from benzene. The procedure gives 5-benzoyl-1,2,3,4-tetrahydro-1-naphthoic acid, melting point: 164°–165°C.

EXAMPLE 13-(6)

In 200 ml. of 1N aqueous sodium hydroxide is dissolved 14 g. of 5-(p-methylbenzyl)-1,2,3,4-tetrahydro-1-naphthoic acid, and a solution of 26 g. of potassium permanganate in 800 ml. of water is added dropwise. After stirring overnight, the reaction mixture is rendered acidic by the addition of concentrated sulfuric acid, followed by the addition of sodium bisulfite. The mixture is extracted with chloroform and the chloroform layer is washed with water and dried over anhydrous magnesium sulfate. The solvent is distilled off under reduced pressure and the oily residue is purified by column chromatography on silica gel equilibrated with oxalic acid and, then, recrystallized from cyclohexane. The described procedure gives 5-(p-toluoyl)-1,2,3,4-tetrahydro-1-naphthoic acid, melting point:

102°–103°C.

EXAMPLE 13-(7)

To 200 ml. of ethyl ether is added 15 g. of 5-(p-chlorobenzyl)-1,2,3,4-tetrahydro-1-naphthoic acid, and a solution of 5 g. of sodium dichromate in 24 ml. of 6N sulfuric acid is added dropwise. After stirring overnight, 100 ml. of water is added and the ethereal layer is further washed with water and dried over anhydrous magnesium sulfate. The solvent is distilled off under reduced pressure and the oily residue is purified by column chromatography on silica gel equilibrated with oxalic acid with chloroform as the eluent and, then, recrystallized from benzene. The described procedure gives 5-(p-chlorobenzoyl)-1,2,3,4-tetrahydro-1-naphthoic acid, melting point: 152.5°–153.5°C.

EXAMPLE 13-(8)

To 100 ml. of acetic acid is added 6.6 g. of 5-benzyl-1,2,3,4-tetrahydro-1-naphthamide and, under cooling with ice, 3.4 g. of chromic anhydride is added. The mixture is stirred well. After stirring overnight, the reaction mixture is poured over 500 g. of ice and the resultant crystals are collected by filtration. This is subjected to column chromtography on silica gel using chloroform as the eluent and the eluate is recrystallized from cyclohexane. The procedure gives 5-benzoyl-1,2,3,4-tetrahydro-1-naphthamide, melting point: 145.5°–147.5°C.

EXAMPLE 13-(9)

To 60 ml. of dioxane are added 6.3 g. of 4-benzylindan-1-carboxylic acid and 2.8 g. of selenium dioxide and the mixture is refluxed for 12 hours. After cooling, water and chloroform are added and the insolubles are filtered off. The filtrate is extracted with chloroform and the chloroform layer is extracted with 5 % aqueous potassium carbonate. The extract is decolorized with activated carbon and rendered acidic with hydrochloric acid. The precipitate is extracted with chloroform and the extract is washed with water and dried. The solvent is distilled off under reduced pressure and the residue is crystallized from a 20:7 solvent mixture of cyclohexane and benzene. The described procedure gives 4-benzoylindan-1-carboxylic acid as crystals melting at 100°–102°C.

EXAMPLES 13-(10) – 13-(12)

By a similar manner to Example 13-(6), the following compounds are produced.

| Example | Produced-compound | Starting compound |
|---|---|---|
| 13-(10) | 4-(p-toluoyl)indan-1-carboxylic acid melting point: 130–131.5°C[benzene-cyclohexane (8:25)] | 4-(p-methylbenzyl)-indan-1-carboxylic acid |
| 13-(11) | 4-(p-chlorobenzoyl)-indan-1-carboxylic acid melting point: 137–139°C[benzene-cyclohexane(3:10)] | 4-(p-chlorobenzyl)-indan-1-carboxylic acid |
| 13-(12) | 4-(p-methoxybenzoyl)-indan-1-carboxylic acid melting point: 136.5–138°C[benzene] | 4-(p-methoxybenzyl)-indan-1-carboxylic acid |

EXAMPLE 13-(13)

To 150 ml. of acetone is added 12.5 g. of 6-benzylindan-1-carboxamide, followed by the dropwise addition of a solution of 5 g. of sodium dichromate in 24 ml. of 6N sulfuric acid. After the addition has been completed, the mixture is stirred overnight. Then, 200 ml. of water is added and the acetone is distilled off under reduced pressure. The residue is extracted with ethyl acetate. The extract is washed with water and dried, followed by removal of the solvent by distillation under reduced pressure. The residue is purified by column chromatography (500 g. of silica gel; eluted with a 7:3 solvent mixture of chloroform and acetone) and the resultant crude crystals are recrystallized from benzene. The procedure gives 6-benzoylindan-1-carboxamide as crystals melting at 195°–197°C.

EXAMPLE 13-(14)

In 100 ml. of acetic acid is dissolved 7.3 g. of ethyl 4-benzylindan-1-carboxylate and, under cooling with ice, 3.4 g. of chromic anhydride is added. After the mixture is stirred overnight, the reaction mixture is poured over 500 g. of ice and extracted with chloroform. The extract is washed with water and dried. The solvent is distilled off under reduced pressure and the residue is purified by column chromatography (700 g. silica gel; eluted with a 40:1 mixture of benzene and ethyl acetate). The procedure gives ethyl 4-benzoylindan-1-carboxylate as an oily product.
Infrared absorption spectrum (neat).
1720 cm$^{-1}$ (ester carbonyl).
1650 cm$^{-1}$ (ketone carbonyl).

EXAMPLE 14-(1)

Sodium ethoxide, prepared from 1.1 g. of sodium metal, is dissolved in a mixture of 24 ml. of dry ethanol and 48 ml. of dry dimethoxyethane and, under cooling with ice-water and stirring, the resultant solution is added dropwise to a 120 ml. of dry dimethoxyethane solution dissolving 9.5 g. of 4-benzoylindan-1-one and 9.4 g. of N-(p-toluenesulfonylmethyl) isonitrile over a period of 20 minutes. After the dropwise addition has been completed, the mixture is further stirred at the same temperature for 30 minutes and at room temperature for 3.5 hours. Following the addition of water, the reaction mixture is extracted with ether and the extract is washed with water and dried. The solvent is distilled of under reduced pressure and the residue is purified by column chromatography on silica gel [1 Kg. of silica gel; eluant: benzene-ethyl acetate (50:1)]. The described procedure gives 4-benzoylindan-1-carbonitrile as an oily product.
Infrared absorption spectrum (neat).
1660 cm$^{-1}$ (carbonyl).
2230 cm$^{-1}$ (nitrile).
Nuclear magnetic resonance spectrum (CDCl$_3$, 60 MHz).
δ : 4.26 (1H, t, C$_1$–H).

EXAMPLES 14-(2) – 14-(10)

By a similar manner to Example 14-(1), the following compounds are obtained.

| Example | Produced-compound | Starting compound |
|---|---|---|
| 14-(2) | 4-(p-toluoyl)indan-1-carbonitrile | 4-(p-toluoyl)indan-1-one |

-continued

| Example | Produced-compound | Starting compound |
|---|---|---|
| | IR 1665 cm$^{-1}$ carbonyl, 2225 cm$^{-1}$(nitrile) | N-(p-toluenesulfonyl-methyl)isonitrile |
| 14-(3) | 4-(p-fluorobenzoyl)-indan-1-carbonitrile IR 1655 cm$^{-1}$ (carbonyl), 2230 cm$^{-1}$ (nitrile) | 4-(p-fluorobenzoyl)-indan-1-one N-(p-toluenesulfonyl-methyl)isonitrile |
| 14-(4) | 4-(p-chlorobenzoyl)-indan-1-carbonitrile melting point: 116–118°C [benzene-cyclohexane(1:10)] | 4-(p-chlorobenzoyl)-indan-1-one N-(p-toluenesulfonyl-methyl)isonitrile |
| 14-(5) | 4-(p-bromobenzoyl)-indan-1-carbonitrile melting point: 114–116°C[benzene-hexane-cyclohexane (3:20:20)] | 4-(p-bromobenzoyl)-indan-1-one N-(p-toluenesulfonyl-methyl)isonitrile |
| 14-(6) | 4-(p-chloro-m-methylbenzoyl)indan-1-carbonitrile oily product IR 1660 cm$^{-1}$ (carbonyl), 2240 cm$^{-1}$ (nitrile) | 4-(p-chloro-m-methyl-benzoyl)indan-1-one N-(p-toluenesulfonyl-methyl)isonitrile |
| 14-(7) | 4-(2,4,6-tri-methyl-benzoyl)indan-1-carbonitrile melting point: 133.5–135°C[cyclo-hexane-hexane] | 4-(2,4,6-trimethyl-benzoyl)indan-1-one N-(p-toluenesulfonyl-methyl)isonitrile |
| 14-(8) | 5-benzoyl-1,2,3,4-tetrahydro-1-naphthonitrile melting point: 91.5–93.5°C[hexane] | 5-benzoyl-3,4-dihydro-1(2H)naphthalenone N-(p-toluenesulfonyl-methyl)isonitrile |
| 14-(9) | 5-(p-toluoyl)-1,2,3,4-tetrahydro-1-naphthonitrile melting point: 72–73°C[hexane] | 5-(p-toluoyl)-3,4-dihydro-1(2H)-naphthalenone N-(p-toluenesulfonyl-methyl)isonitrile |
| 14-(10) | 5-(p-chlorobenzoyl)-1,2,3,4-tetrahydro-1-naphthonitrile melting point: 97–99°C[hexane] | 5-(p-chlorobenzoyl)-3,4-dihydro-1(2H)-naphthalenone N-(p-toluenesulfonyl-methyl)isonitrile |

EXAMPLE 14-(11)

Sodium ethoxide, prepared from 1.4 g. of sodium metal, is dissolved in a mixture of 30 ml. of dry ethanol and 60 ml. of dry dimethoxyethane and, under cooling with ice and stirring, the resultant solution is added dropwise to a 150 ml. of dry dimethoxyethane solution dissolving 8.2 g. of ethyl 1-oxoindan-4-carboxylate and 12 g. of N-(p-toluenesulfonylmethyl)isonitrile over a period of 35 minutes. After the dropwise addition has been completed, the mixture is stirred at the same temperature for 35 minutes and, then, at room temperature for 5.5 hours. Following the addition of water, the reaction mixture is extracted with ether and the extract is washed with water and dried. The solvent is distilled off under reduced pressure and the residue is purified by column chromatography on silica gel (1 Kg. of silica gel; eluant: benzene-ethyl acetate (50:1)). Recrystallization from cyclohexane gives ethyl 1-cyanoindan-4-carboxylate as crystals melting at 93°–95.5°C.

EXAMPLE 14-(12)

By a similar manner to Example 14-(11), ethyl ester of 1-cyano-1,2,3,4-tetrahydro-5-naphthoic acid is produced as an oily substance from ethyl ester of 1,2,3,4-tetrahydro-1-oxo-5-naphthoic acid and N-(p-toluenesulfonylmethyl)isonitrile.
Infrared absorption spectrum (neat).
1720 cm$^{-1}$ (carbonyl), 2240 cm$^{-1}$ (nitrile).

Nuclear magnetic resonance spectrum (CDCl$_3$, 100 MHz).
δ : 1.36(3H, t, —CH$_3$), 4.00(1H, t, C$_1$—H), 4.33(2H, q, O—CH$_2$—)

EXAMPLE 14-(13)

In 80 ml. of dry dimethoxyethane are dissolved 5.2 g. of 4-(p-chlorobenzyl)indan-1-one and 6 g. of N-(p-toluenesulfonylmethyl)isonitrile and while the solution is stirred under cooling with ice, a solution of 0.72 g. of sodium metal in a solvent mixture of 20 ml. of dry ethanol and 40 ml. of dry dimethoxyethane is added dropwise over a period of about 30 minutes. After the drop-by-drop addition has been completed, the mixture is stirred under cooling with ice for 1 hour and, then, at room temperature for 3 hours. After the reaction has been completed, 800 ml. of dilute hydrochloric acid are added, followed by extraction with ether. The extract is washed with aqueous sodium chloride and dried. The solvent is distilled off under reduced pressure and the residue is purified by column chromatography (600 g. of silica gel; elution with a 100:1 mixture of benzene and ethyl acetate). The described procedure gives 4-(p-chlorobenzyl)indan-1-carbonitrile as an oily product.
Infrared absorption spectrum (neat).
2250 cm$^{-1}$ (nitrile).
Nuclear magnetic resonance spectrum (CDCl$_3$ solution, 60 MHz).
δ : 2.0–3.0 (4H, m, —CH$_2$—CH$_2$—).
δ : 3.85 (2H, s, Ar—CH$_2$—Ar).
δ : 4.02 (1H, t, >CH—CN).
δ : 6.8–7.4 (7H, m, aromatic protons).

EXAMPLES 14-(14) – 14-(16)

By a similar manner to Example 14-(13), the following compounds are produced.

| Example | Produced-compound | Starting compound |
|---|---|---|
| 14-(14) | 4-benzylindan-1-carbonitrile melting point: 43–44.5°C [n-hexane] | 4-benzylindan-1-one |
| 14-(15) | 4-(p-methylbenzyl)-indan-1-carbonitrile melting point: 60–62°C [n-hexane] | 4-(p-methylbenzyl)-indan-1-one |
| 14-(16) | 4-(p-methoxybenzyl)-indan-1-carbonitrile NMR(CDCl$_3$, 100MHz) δ:2.2–3.0(4H,m,—CH$_2$—CH$_2$—), 3.63(3H,s, —OCH$_3$), 3.80(2H,s, φ—CH$_2$—Ar), 3.96(1H, t, >CH—Cl) 6.7–7.3 (7H,m,aromatic) | 4-(p-methoxybenzyl)-indan-1-one |

EXAMPLE 15-(1)

In 50 ml. of ether is dissolved 2.7 g. of 4-benzoylindan-1-carboxylic acid and, then, an ethereal solution of diazomethane is added until the yellow color of the solution has not disappeared. The solution is then allowed to stand for 30 minutes, after which the excess diazomethane and the ether are distilled off. The methyl 4-benzoylindan-1-carboxylate thus obtained as the distillation residue is dissolved in 50 ml. of dimethylsulfoxide and under stirring, the solution is added dropwise to 100 ml. of dimethylsulfoxide containing 1.5 g. of sodium hydride over a period of 15 minutes.

After the dropwise addition has been completed, the mixture is further stirred for 2.5 hours and, then, a solution of 15.0 g. of methyl iodide in 30 ml. of dimethylsulfoxide is added dropwise over a period of 30 minutes. After the dropwise addition has been completed, the mixture is further stirred for 2.0 hours. The mixture is rendered acidic with dilute hydrochloric acid and, then, extracted with ether. The extract is washed with water and dried. Then, the solvent is distilled off under reduced pressure and the residue is purified by column chromatography on silica gel(300 g. silica gel; eluted with a 40:1 mixture of benzene and ethyl acetate). The described procedure gives methyl 4-benzoyl-1-methyl-indan-1-carboxylate as an oily product.

Elemental analysis: $C_{19}H_{18}O_3$. Calcd. C, 77.53; H, 6.16. Found C, 77.34; H, 6.10.

EXAMPLE 15-(2)

By a similar manner to Example 15-(1), the following compounds are produced.

| Example | Produced-compound | Starting compound |
|---------|-------------------|-------------------|
| 15-(2)  | 4-benzoyl-1-methyl-indan-1-carboxamide melting point: 109–110 °C[benzene-hexane (1:1)] | 4-benzoylindan-1-carboxamide methyl iodide |

EXAMPLE 15-(3)

In 50 ml. of ether is dissolved 3.0 g. of 4-(p-chlorobenzoyl)indan-1-carboxylic acid and the esterification is carried out by adding an ethereal solution of diazomethane.

The excess diazomethane and the ether are distilled off under reduced pressure. The resultant methyl 4-(p-chlorobenzoyl)indan-1-carboxylate is dissolved in 50 ml. of dimethylsulfoxide and under stirring, the solution is added dropwise to 100 ml. of dimethylsulfoxide containing 1.5 g. of sodium hydride over a period of 15 minutes. After the dropwise addition has been completed, the mixture is stirred for 3.0 hours and, then, a solution of 15.0 g. of methyl iodide in 30 ml. of dimethylsulfoxide is added dropwise over 25 minutes. After the dropwise addition has been completed, the mixture is further stirred for 2.0 hours.

It is then rendered acidic with dilute hydrochloric acid and extracted with ether. The extract is washed with water and dried. The solvent is then distilled off under reduced pressure and the residue is purified by column chromatography (300 g. silica gel; eluted with a 40:1 mixture of benzene and ethyl acetate). The procedure gives methyl 4-(p-chlorobenzoyl)-1-methyl-indan-1-carboxylate as an oily product. This product is dissolved in a solvent mixture of 35 ml. ethanol and 35 ml. water and, then, 1.6 g. of potassium hydroxide is added. The mixture is refluxed for 2 hours, after which the ethanol is distilled off. Following the addition of 100 ml. of water, the residue is washed with ether. The water layer is rendered acidic with hydrochloric acid and the resultant precipitate is extracted with chloroform. The extract is washed with water and dried. The solvent is then distilled off under reduced pressure and the residue is crystallized from a 7:20 mixture of benzene and hexane. The procedure gives 4-(p-chlorobenzoyl)-1-methylindan-1-carboxylic acid as colorless crystals melting at 146.5°–149.5°C.

EXAMPLE 15-(4)

In 50 ml. of ether is dissolved 2.8 g. of 4-(p-toluoyl)-indan-1-carboxylic acid and the esterification is carried out by adding an ethereal solution of diazomethane.

The excess diazomethane and the ether are distilled off under reduced pressure. The resultant methyl 4-(p-toluoyl)indan-1-carboxylate is dissolved in 50 ml. of dimethylsulfoxide and under stirring, the solution is added dropwise to 100 ml. of dimethylsulfoxide containing 1.0 g. of sodium hydride over a period of 15 minutes. After the dropwise addition has been completed, the mixture is stirred for 2.5 hours and, then, a solution of 15.0 g. methyl iodide in 30 ml. dimethylsulfoxide is added drop by drop over a period of 25 minutes. After the dropwise addition has been completed, the mixture is further stirred for 2.5 hours. It is then rendered acidic with dilute hydrochloric acid and extracted with ether. The extract is washed with water and dried. Finally the solvent is distilled off under reduced pressure and the residue is purified by column chromatography (300 g. silica gel; eluted with a 40:1 mixture of benzene and ethyl acetate). The procedure gives methyl 4-(p-toluoyl)-1-methylindan-1-carboxylate as an oily product. This product is dissolved in a solvent mixture of 35 ml. ethanol and 35 ml. water and, then, 1.5 g. of potassium hydroxide is added. The mixture is refluxed for 2 hours, after which time the ethanol is distilled off under reduced pressure. Following the addition of 100 ml. of water, the residue is washed with ether. The water layer is rendered acidic with hydrochloric acid and the precipitate is extracted with chloroform. The extract is washed with water and dried.

Finally the solvent is distilled off under reduced pressure and the residue is crystallized from a 1:4 mixture of benzene and hexane. The described procedure gives 4-(p-toluoyl)-1-methylindan-1-carboxylic acid as crystals melting at 99°–101°C.

EXAMPLE 16-(1)

In 35 ml. of ethanol is dissolved 1.5 g. of ethyl 4-benzoylindan-1-carboxylate, followed by the addition of a solution of 800 mg. of potassium hydroxide in 35 ml. of water. The mixture is heated on reflux for 2 hours, after which it is concentrated under reduced pressure.

The residue is dissolved in 300 ml. of water and the water layer is washed with ether and made acidic with hydrochloric acid. The precipitate is extracted with chloroform and the organic layer is washed with water and dried over anhydrous sodium sulfate. Then, the solvent is distilled off, which leaves an oil of 4-benzoyl-indan-1-carboxylic acid. This product is dissolved in a 7:20 solvent mixture of benzene and cyclohexane and the solution is allowed to stand, whereupon crystals separate out gradually, melting point:101.5°–103°C.

EXAMPLE 16-(2)

To 500 ml. of concentrated hydrochloric acid is added 15.9 g of 4-benzoylindan-1-carboxamide and the mixture is refluxed for 5 hours. After cooling, the solution is extracted with chloroform and the chloroform layer is washed with water and extrated with a 1N aqueous solution of sodium hydroxide. The extract is decolorized with activated carbon and rendered acidic by the addition of hydrochloric acid, followed by extraction with chloroform. The extract is washed with water and a saturated aqueous solution of sodium chloride and, then, dried.

The solvent is distilled off under reduced pressure and the residue is crystallized from benzene-cyclohexane (7:20). The described procedure gives 4-benzoylindan-1-carboxylic acid as crystals melting at 100.5°–102°C.

EXAMPLE 16-(3)

To 13.3 g. of 4-benzoylindan-1-carboxylic acid is added 50 ml. of thionyl chloride and the mixture is left standing at room temperature overnight. Then, the excess thionyl chloride is distilled off under reduced pressure. Ether is added to the residue and, then, ammonia gas is bubbled through the reaction mixture. The resultant precipitate is recovered by filtration, washed with water and dried. Recrystallization from benzene gives 4-benzoylindan-1-carboxamide as crystals melting at 164°–166°C.

EXAMPLE 16-(4)

To 250 ml. of ethanol is added 20 ml. of concentrated sulfuric acid, followed by the addition of 13.3 g. of 4-benzoylindan-1-carboxylic acid. The mixture is refluxed for 5.5 hours. After cooling, the ethanol is distilled off under reduced pressure and water is added to the residue, followed by extraction with ether. The ethereal layer is washed with a 5 % aqueous solution of sodium hydroxide and a saturated aqueous solution of sodium chloride and, then, dried. The solvent is distilled off under reduced pressure and the residue is purified by column chromatography on silica gel (eluted with chloroform). The described procedure gives ethyl 4-benzoylindan-1-carboxylate as an oily product.

Infrared absorption spectrum (neat).
1720 cm$^{-1}$ (ester carbonyl).
1650 cm$^{-1}$ (ketone carbonyl).

EXAMPLE 16-(5)

To 3 g. of 4-benzoylindan-1-carboxylic acid are added 25 ml. of chloroform and 25 ml. of thionyl chloride. The mixture is allowed to stand overnight and, then, the excess thionyl chloride and the solvent are distilled off under reduced pressure. To the acid chloride thus obtained is added 50 ml. of benzene. Then, 50 ml. of water, 7.0 g. of hydroxylamine hydrochloride and 4.0 g. of sodium hydroxide are further added. The mixture is stirred at room temperature for 4 hours. Following the addition of water, the reaction mixture is extracted with ethyl acetate and the extract is washed with water and dried. The solvent is then distilled off under reduced pressure and the residue is recrystallized from benzene. The procedure gives N-hydroxy-4-benzoylindan-1-carboxamide as crystals melting at 159.5°–160.5°C.

EXAMPLE 16-(6)

To 3.0 g. of 4-benzoylindan-1-carboxylic acid are added 25 ml. of chloroform and 25 ml. of thionyl chloride. The mixture is allowed to stand at room temperature overnight and, then, the excess thionyl chloride and the solvent are distilled off under reduced pressure. To the acid chloride thus obtained are added 50 ml. of benzene and 10 ml. of aqueous methylamine solution (40 %). The mixture is stirred at room temperature for 4 hours, after which water is added, followed by extraction with ethyl acetate. The extract is washed with water and dried. Finally the solvent is distilled off under reduced pressure and the residue is crystallized from a mixture of benzene and ether. The procedure gives N-methyl-4-benzoylindan-1-carboxamide as crystals melting at 145°–146.5°C.

EXAMPLE 16-(7)

To 3.0 g. of 4-benzoylindan-1-carboxylic acid are added 25 ml. of chloroform and 25 ml. of thionyl chloride. The mixture is allowed to stand at room temperature overnight and the excess thionyl chloride and the solvent are distilled off under reduced pressure. To the acid chloride thus obtained are added 50 ml. of benzene and 5 ml. of morpholine, followed by stirring at room temperature overnight.

Then, water is added and the mixture is extracted with benzene. The extract is washed with 1N hydrochloric acid and, then, with water and dried. The solvent is distilled off under reduced pressure and the residue is purified by column chromatography (300 g. silica gel, eluted with a 100:3 mixture of chloroform and acetone). The procedure gives 4-benzoylindan-1-carboxyl morpholide as an oily product.

Infrared absorption spectrum (neat).
1655 cm$^{-1}$ (amide and ketone).

EXAMPLE 16-(8)

In a solution of 450 mg. of sodium hydroxide in 20 ml. of water, there is dissolved 3.35 g. of 4-benzoylindan-1-carboxylic acid and the insolubles are filtered off. To the filtrate is added a solution of 950 mg. of aluminum chloride hexahydrate in 100 ml. of water and the mixture is stirred for 3 hours. The resultant crystals are collected by filtration, washed with water, dried and washed with ether. The procedure gives aluminum tris(4-benzoylindan-1-carboxylate) is obtained as crystals melting at 225°–230°C.

EXAMPLE 16-(9)

In 50 ml. of ether is dissolved 2.66 g. of 4-benzoylindan-1-carboxylic acid. To this is added an ethanolic solution of sodium ethoxide prepared from 230 mg. of sodium metal and 10 ml. of ethanol. The mixture is allowed to stand for 20 minutes, after which time the solvent is distilled off under reduced pressure.

The resultant powder is washed with acetone, whereupon sodium 4-benzoylindan-1-carboxylate is obtained as a powder melting at 238°–240°C (in a sealed tube).

EXAMPLE 16-(10)

To 14.0 g. of 4-(p-toluoyl)indan-1-carboxamide is added 500 ml. of concentrated hydrochloric acid and the mixture is refluxed for 3.5 hours. After cooling, the mixture is extracted with chloroform and the chloroform layer is washed with water and extracted with a 5 % aqueous solution of potassium carbonate. The extract is decolorized with activated carbon and rendered acidic with hydrochloric acid. The precipitate is extracted with chloroform. The extract is washed with water and dried. The solvent is distilled off under reduced pressure and the residue is crystallized from an 8:25 mixture of benzene and cyclohexane. The described procedure gives 4-(p-toluoyl)indan-1-carboxylic acid as crystals melting at 130°–131.5°C.

EXAMPLES 16-(11) – 16-(14)

By a similar manner to Example 16-(2), the following compounds are produced.

| Example | Produced-compound | Starting compound |
|---|---|---|
| 16-(11) | 4-(p-methoxybenzoyl)-indan-1-carboxylic acid<br>melting point: 137.5–138.5°C [benzene] | 4-(p-methoxybenzoyl)-indan-1-carboxamide |
| 16-(12) | 5-benzoyl-1,2,3,4-tetrahydro-1-naphthoic acid<br>melting point: 164–165°C[benzen] | 5-benzoyl-1,2,3,4-tetrahydro-1-naphthamide |
| 16-(13) | 5-(p-chlorobenzoyl)-1,2,3,4-tetrahydro-1-naphthoic acid<br>melting point: 152.5–153.5°C [benzene-hexane] | 5-(p-chlorobenzoyl)-1,2,3,4-tetrahydro-1-naphthamide |
| 16-(14) | 4-(2,4,6-trimethylbenzoyl)indan-1-carboxylic acid<br>melting point: 191.5–193°C[benzene-cyclohexane(1:1)] | 4-(2,4,6-trimethylbenzoyl)indan-1-carboxamide |

EXAMPLE 16-(14)

To 500 ml. of concentrated hydrochloric acid is added 17.6 g. of 5-(p-toluoyl)-1,2,3,4-tetrahydro-1-naphthamide and the mixture is refluxed for 5 hours. After cooling, it is extracted with chloroform and the chloroform layer is washed with water and extracted with 1N sodium hydroxide. The extract is decolorized with activated carbon, rendered acidic with hydrochloric acid and extracted with chloroform. The chloroform layer is washed with water and dried. The solvent is distilled off under reduced pressure and the crystalline residue is recrystallized from benzene. The procedure gives 5-(p-toluoyl)-1,2,3,4-tetrahydro-1-naphthoic acid, melting point: 102°–103°C.

EXAMPLE 17-(1)

To 60 ml. of acetone are added 3.2 g. of 4-benzoylindan-1-carboxylic acid and 1.70 g. of cinchonidine and the mixture is shaken to dissolve. The solution is allowed to stand at room temperature overnight and the resultant crystlas are recovered by filtration and recrystallized twice from acetone. The procedure gives l-4-benzoylindan-1-carboxylic acid cinchonidine salt as colorless crystals melting at 189°–192°C, $[\alpha]_D^{22}$ -132.2° (c=1, $CHCl_3$).

This product is dissolved in chloroform and the solution is shaken twice with portions of dilute hydrochloric acid to remove the cinchonidine.

The chloroform layer is washed with water and dried over magnesium sulfate. The solvent is distilled off under reduced pressure. The procedure gives l-4-benzoylindan-1-carboxylic acid as a colorless oil, $[\alpha]_D^{22}$-66.4° (c=1, MeOH).

The mother liquor after harvest of the first crop of crystals is concentrated under reduced pressure and the residue is shaken with 1.7 g. of cinchonidine and 120 ml. of acetonitrile under stirring and heating, after which the mixture is allowed to stand at room temperature overnight. The resultant crystals are collected by filtration and recrystallized three times from acetonitrile. The described procedure gives d-4-benzoylindan-1-carboxylic acid cinchonidine salt as colorless crystals melting at 180°–183°C, $[\alpha]_D^{22}$ 11.2°(c=1, $CHCl_3$).

This product is dissolved in chloroform and the solution is shaken twice with portions of hydrochloric acid to remove the cinchonidine. The chloroform layer is washed with water and dried over magnesium sulfate. Finally, the solvent is distilled off under reduced pressure to obtain d-4-benzoylindan-1-carboxylic acid as a colorless oil, $[\alpha]_D^{22}$ 66.4° (c=1, MeOH).

EXAMPLE 17-(2)

To 100 ml. of acetone are added 3.1 g. of 4-(p-chlorobenzoyl)indan-1-carboxylic acid and 1.5 g. of cinchonine and the mixture is warmed to dissolve. Then, with the addition of a small amount of activated carbon, the solution is filtered. The filtrate is allowed to stand at room temperature overnight and, then, at 0°–5°C for another night. The crystals formed are recovered by filtration and recrystallized from acetonitrile. The described procedure gives l-4-(p-chlorobenzoyl)indan-1-carboxylic acid cinchonine salt as colorless crystals, melting point: 193°–196°C, $[\alpha]_D^{23}$ 33.6° (c=1, $CHCl_3$).

The above product is dissolved in chloroform and the solution is shaken twice with portions of dilute hydrochloric acid to remove the cinchonine. The chloroform layer is washed with water and dried over magnesium sulfate. The solvent is distilled off under reduced pressure, and cyclohexane is added to the residue. The resultant crystals are collected by filtration and recrystallized from a 1:4 mixture of benzene and cyclohexane. The procedure gives l-4-(p-chlorobenzoyl)indan-1-carboxylic acid as colorless crystals melting at 121°–122°C. $[\alpha]_D^{24}$ –66.9° (c=1, MeOH)

EXAMPLE 17-(3)

In 100 ml. of acetone are dissolved 3.1 g. of 4-(p-chlorobenzoyl)indan-1-carboxylic acid and 1.5 g. of cinchonine under heating and, with the addition of a small amount of activated carbon, the solution is filtered. The filtrate is allowed to stand at room temperature overnight and, then, at 0°–5°C again overnight. The resultant crystals are filtered off. The filtrate is concentrated under reduce pressure and the residue is dissolved in 50 ml. of acetonitrile. The solution is allowed to stand for a week and the crystals formed are filtered off. The filtrate is concentrated under reduced pressure and the residue is dissolved in 150 ml. of chloroform. The solution is washed twice with dilute hydrochloric acid and once with water, and dried by the addition of magnesium sulfate. The solvent is distilled off under reduced pressure and the residue is dissolved in 80 ml. of acetonitrile, followed by the addition of 0.6 g. of l-α-phenethylamine. The mixture is allowed to stand overnight and the resultant crystals are collected by filtration and recrystallized five times from acetonitrile.

The described procedure gives d-4-(p-chlorobenzoyl)-indan-1-carboxylic acid l-α-phenethylamine salt as colorless crystals melting at 148°–150°C. $[\alpha]_D^{24}$ 62.2° (c=1, $CHCl_3$).

This product is dissolved in 150 ml. of chloroform and the solution is washed twice with dilute hydrochloric acid and once with water and dried by the addition of magnesium sulfate. The solvent is distilled off under reduced pressure and cyclohexane is added to the residue. The resultant crystals are collected by filtration and recrystallized twice from a 1:4 mixture of benzene and cyclohexane. The procedure gives d-4-(p-chlorobenzoyl)indan-carboxylic acid as colorless crystals melting at 121°–122°C, $[\alpha]_D^{24}$ 65.0° (c=1, MeOH).

What is claimed is:

1. A compound of general formula

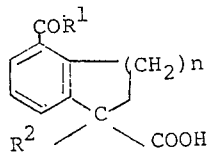

wherein $R^1$ is a naphthyl or phenyl group which is unsubstituted or substituted by a lower alkyl having 1 to 4 carbon atoms, a lower alkoxy having 1 to 4 carbon atoms, a halogen, a mono- or di-alkylamino having 1 to 3 carbon atoms, acetylamino, propionylamino, acetyloxy or propionyloxy; $R^2$ is hydrogen or a lower alkyl group having 1 to 4 carbon atoms and n is 1 or 2; or an alkyl ester whose alkyl moiety has 1 to 6 carbon atoms, phenyl ester, benzyl ester, or pharmaceutically acceptable salt thereof at the carboxyl function thereof.

2. A compond claimed in claim 1, wherein $R^2$ is hydrogen.

3. A compound claimed in claim 1, wherein $R^2$ is a lower alkyl group having 1 to 4 carbon atoms.

4. A compound claimed in claim 1, wherein $n$ is 1.

5. A compound claimed in claim 1, wherein $n$ is 2.

6. A compound claimed in claim 1, wherein $R^1$ is a phenyl or naphthyl group which is unsubstituted.

7. A compound claimed in claim 1, wherein $R^1$ is a phenyl or naphthyl group which is substituted by a lower alkyl having 1 to 4 carbon atoms, a lower alkoxy having 1 to 4 carbon atoms, a halogen, a mono- or di-alkylamino having 1 to 3 carbon atoms, acetylamino, propionylamino, acetyloxy or propionyloxy.

8. A compound claimed in claim 1, wherein $R^1$ is a phenyl group which is unsubstituted or substituted by a lower alkyl having 1 to 4 carbon atoms, a lower alkoxy having 1 to 4 carbon atoms, a halogen, a mono- or di-alkylamino having 1 to 3 carbon atoms, acetylamino, propionylamino, acetyloxy or propionyloxy.

9. A compound claimed in claim 1, wherein $R^1$ is phenyl which is unsubstituted or substituted by a lower alkyl having 1 to 4 carbon atoms, a lower alkoxy having 1 to 4 carbon atoms, a halogen, a mono- or di-alkylamino having 1 to 3 carbon atoms, acetylamino, propionylamino, acetoxy or propionyloxy; $R^2$ is hydrogen and $n$ is 1.

10. A compound claimed in claim 1, wherein the compound is 4-benzoylindan-1-carboxylic acid.

11. A compound claimed in claim 1, wherein the compound is 4-(p-chlorobenzoyl)indan-1-carboxylic acid.

12. A compound claimed in claim 1, wherein the compound is 4-(p-toluoyl)indan-1-carboxylic acid.

13. A compound claimed in claim 1, wherein the compound is 4-(p-methoxybenzoyl)indan-1-carboxylic acid.

14. A compound claimed in claim 1, wherein the compound is 5-benzoyl-1,2,3,4-tetrahydro-1-naphthoic acid.

15. A compound claimed in claim 1, wherein the compound is 5-(p-chlorobenzoyl)-1,2,3,4-tetrahydro-1-naphthoic acid.

16. A compound claimed in claim 1, wherein the compound is 5-(p-toluoyl)-1,2,3,4-tetrahydro-1-naphthoic acid.

17. A compound claimed in claim 1, wherein the compound is 4-benzoyl-1-methylindan-1-carboxylic acid.

18. A compound claimed in claim 1, wherein the compound is 4-(p-toluoyl)-1-methylindan-1-carboxylic acid.

19. A compound claimed in claim 1, wherein the compound is 4-(p-chlorobenzoyl)-1-methylindan-1-carboxylic acid.

20. A compound claimed in claim 1, wherein pharmaceutically acceptable salt is alkali metal salt, alkaline earth metal salt, aluminum salt, ammonium salt or organic amine salt.

* * * * *